(12) United States Patent
Yuan et al.

(10) Patent No.: US 11,585,757 B2
(45) Date of Patent: Feb. 21, 2023

(54) DEVICE FOR LUMINESCENT IMAGING

(71) Applicant: Illumina, Inc., San Diego, CA (US)

(72) Inventors: Dajun Yuan, San Diego, CA (US); Liangliang Qiang, San Diego, CA (US); Minghao Guo, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 717 days.

(21) Appl. No.: 16/439,635

(22) Filed: Jun. 12, 2019

(65) Prior Publication Data

US 2019/0383741 A1 Dec. 19, 2019

Related U.S. Application Data

(60) Provisional application No. 62/684,907, filed on Jun. 14, 2018.

(30) Foreign Application Priority Data

Jul. 5, 2018 (NL) ..................................... 2021258

(51) Int. Cl.
*G01N 21/64* (2006.01)
*G02F 1/1335* (2006.01)
(Continued)

(52) U.S. Cl.
CPC ..... *G01N 21/6428* (2013.01); *G01N 21/6454* (2013.01); *G01N 21/6456* (2013.01);
(Continued)

(58) Field of Classification Search
CPC ........... G01N 21/6428; G01N 21/6454; G01N 21/6456; G01N 2201/0635;
(Continued)

(56) References Cited

U.S. PATENT DOCUMENTS 3,856,986 A 12/1974 Macovski
4,213,706 A 7/1980 Hill et al.
(Continued)

FOREIGN PATENT DOCUMENTS

CN 1292227 C 12/2006
CN 101072996 11/2007
(Continued)

OTHER PUBLICATIONS

Frohn, J. , et al., "Three-dimensional resolution enhancement in fluorescence microscopy by harmonic excitation", Pptics Letters 26 (11), 2001, 828-830.

(Continued)

*Primary Examiner* — Blake C Riddick
(74) *Attorney, Agent, or Firm* — Illumina, Inc.

(57) ABSTRACT

A device includes a plurality of imaging pixels in a spatial pattern with a formation of features disposed over the pixels. A first and a second feature of the formation of features are disposed over a first pixel. A first luminophore is disposed within or over the first feature. A second luminophore is disposed within or over the second feature. A structured illumination source is to direct at least a portion of first photons in an illumination pattern to the first feature at a first time, and to direct at least a portion of second photons in the illumination pattern to the second feature at a second time. The structured illumination source includes an illumination pattern generator having an illumination pattern generator actuator connected to the illumination pattern generator to cause the illumination pattern to translate or rotate relative to the formation of features.

24 Claims, 16 Drawing Sheets

(51) Int. Cl.
*G02B 26/00* (2006.01)
*C12Q 1/6869* (2018.01)

(52) U.S. Cl.
CPC ..... *G02F 1/133614* (2021.01); *C12Q 1/6869* (2013.01); *G01N 2021/6439* (2013.01); *G01N 2201/0635* (2013.01); *G02B 26/00* (2013.01)

(58) Field of Classification Search
CPC ........... G02F 1/133614; C12Q 1/6869; G01M 2021/6439; G02B 26/00
See application file for complete search history.

(56) References Cited

U.S. PATENT DOCUMENTS

| | | | |
|---|---|---|---|
| 5,327,515 A * | 7/1994 | Anderson | G02B 6/02138 359/566 |
| 5,510,230 A * | 4/1996 | Tennant | G03F 7/70233 430/311 |
| 5,666,395 A * | 9/1997 | Tsukamoto | G01T 1/2928 250/580 |
| 5,761,085 A | 6/1998 | Giorgio | |
| 6,188,478 B1 | 2/2001 | Fuchs et al. | |
| 6,272,207 B1 * | 8/2001 | Tang | G21K 1/025 378/154 |
| 6,898,004 B2 | 5/2005 | Shimizu et al. | |
| 6,947,127 B2 | 9/2005 | Wolleschensky et al. | |
| 7,274,446 B2 | 9/2007 | Wolleschensky et al. | |
| 7,495,225 B2 * | 2/2009 | Hefetz | G01T 1/2928 250/370.09 |
| 7,532,323 B2 | 5/2009 | Tang et al. | |
| 7,803,609 B2 | 9/2010 | Kaplan | |
| 8,160,379 B2 | 4/2012 | Schaefer et al. | |
| 8,222,040 B2 | 7/2012 | Hong et al. | |
| 8,502,867 B2 | 8/2013 | Park | |
| 8,509,879 B2 | 8/2013 | Durkin et al. | |
| 8,759,077 B2 | 6/2014 | Hong et al. | |
| 8,796,185 B2 | 8/2014 | Kim et al. | |
| 8,817,362 B2 | 8/2014 | Lee | |
| 8,848,199 B2 | 9/2014 | Choi et al. | |
| 9,458,501 B2 | 10/2016 | Hong et al. | |
| 9,465,228 B2 | 10/2016 | Lee et al. | |
| 9,772,505 B2 | 9/2017 | Lee et al. | |
| 10,378,053 B2 | 8/2019 | Staker et al. | |
| 10,429,665 B2 | 10/2019 | Lee et al. | |
| 2001/0016361 A1 | 8/2001 | Seul et al. | |
| 2003/0007732 A1 | 1/2003 | Ronnekleiv | |
| 2003/0128338 A1 * | 7/2003 | Hirata | G03B 21/60 353/31 |
| 2004/0263841 A1 | 12/2004 | Caracci et al. | |
| 2005/0239115 A1 | 10/2005 | Ryu et al. | |
| 2006/0134530 A1 * | 6/2006 | Park | G03F 1/34 430/311 |
| 2007/0023686 A1 * | 2/2007 | Wolleschensky | G02B 21/0076 250/458.1 |
| 2008/0020938 A1 | 1/2008 | Kaplan | |
| 2009/0112482 A1 | 4/2009 | Sandstrom | |
| 2009/0218514 A1 * | 9/2009 | Klunder | G01N 21/6452 250/459.1 |
| 2009/0219607 A1 | 9/2009 | Saggau et al. | |
| 2009/0225407 A1 | 9/2009 | Nakayama et al. | |
| 2009/0238449 A1 | 9/2009 | Zhang et al. | |
| 2009/0250632 A1 | 10/2009 | Kempe et al. | |
| 2010/0051788 A1 | 3/2010 | Klunder et al. | |
| 2010/0096563 A1 * | 4/2010 | Ponjee | G01J 3/0224 250/459.1 |
| 2011/0036996 A1 | 2/2011 | Wolleschensky et al. | |
| 2011/0204209 A1 * | 8/2011 | Barrows | G02B 27/58 250/214.1 |
| 2011/0287387 A1 | 11/2011 | Chen et al. | |
| 2012/0140883 A1 * | 6/2012 | Iwakiri | A61B 6/4291 378/62 |
| 2013/0079232 A1 | 3/2013 | Kain et al. | |
| 2014/0162349 A1 * | 6/2014 | Yamamoto | G01B 9/02041 435/288.7 |
| 2015/0005364 A1 | 2/2015 | Zaccarin et al. | |
| 2015/0053641 A1 | 2/2015 | Zaccarin et al. | |
| 2015/0182178 A1 * | 7/2015 | Baturin | A61B 6/4291 378/36 |
| 2015/0238135 A1 | 8/2015 | Bambot et al. | |
| 2016/0189387 A1 * | 6/2016 | Kannan | G01B 11/2545 382/106 |
| 2016/0273034 A1 | 9/2016 | Lundquist et al. | |
| 2016/0349702 A1 * | 12/2016 | Sung | G03H 1/2294 |
| 2017/0274374 A1 * | 9/2017 | Bowen | B01J 19/0046 |
| 2017/0275690 A1 * | 9/2017 | Dehlinger | G01N 21/6428 |
| 2018/0080885 A1 * | 3/2018 | Ginsberg | G01N 23/22 |
| 2018/0164571 A1 | 6/2018 | Ouchi et al. | |
| 2019/0064066 A1 * | 2/2019 | Lim | C12Q 1/04 |
| 2019/0170904 A1 * | 6/2019 | Topolancik | G01N 21/6458 |

FOREIGN PATENT DOCUMENTS

| | | |
|---|---|---|
| JP | 2005080181 | 3/2005 |
| JP | 2009503442 | 1/2009 |
| KR | 20040001590 | 1/2004 |
| WO | 2006/061783 | 6/2006 |
| WO | 2007/009812 | 1/2007 |
| WO | 2009/100830 | 8/2009 |
| WO | 2016/199179 | 12/2016 |
| WO | 2017/184997 | 10/2017 |
| WO | 2019136290 A1 | 7/2019 |

OTHER PUBLICATIONS

Frohn, J., et al., "True optical resolution beyond the Rayleigh limit achieved by standing wave illumination", PNAS 97 (13), 2000, 7232-7236.

Krishnamurthi, V., et al., "Image processing in 3D standing-wave fluorescence microscopy", Three-Dimensional Microscopy: Image Acquisition and Processing III vol. 2655, International Society for Optics and Photonics, 1996, 18-25.

He, J., et al., "Polarization control in flexible interference lithography for nano-patterning of different photonic structures with optimized contrast", Optics Express, May 4, 2015, 11518-11525.

Van Wolferen, H., et al., "Laser interference lithography", Lithography: Principles, Processes and Materials, Theodore Hennessy, Ed., Nova Science Publishers, Inc., 2011, 133-148.

* cited by examiner

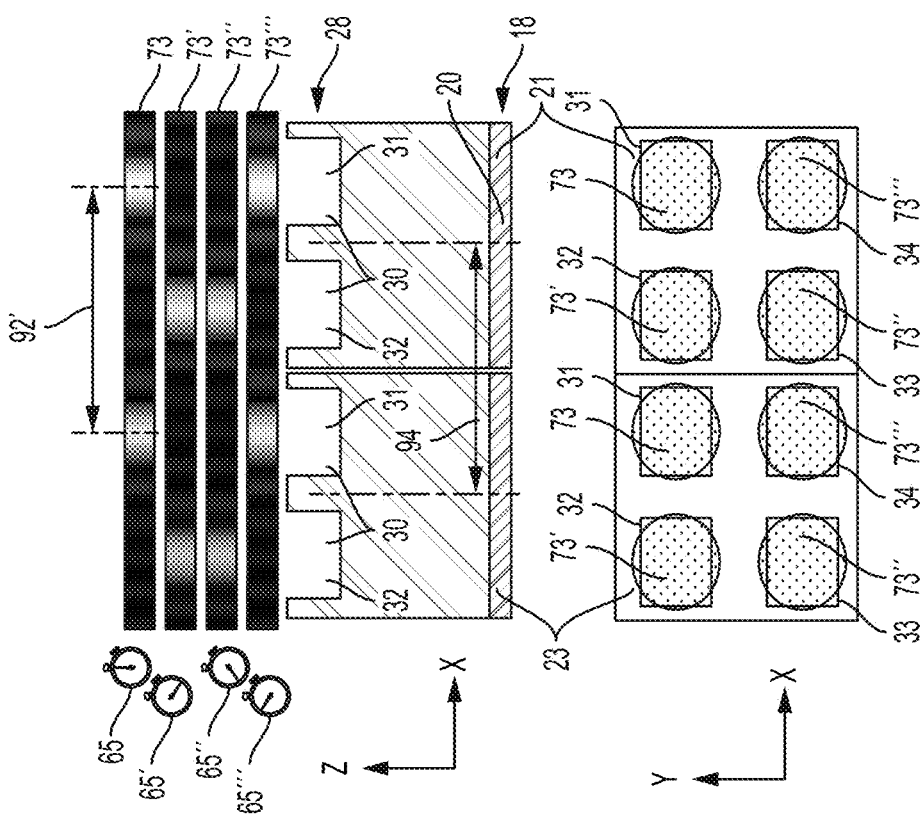
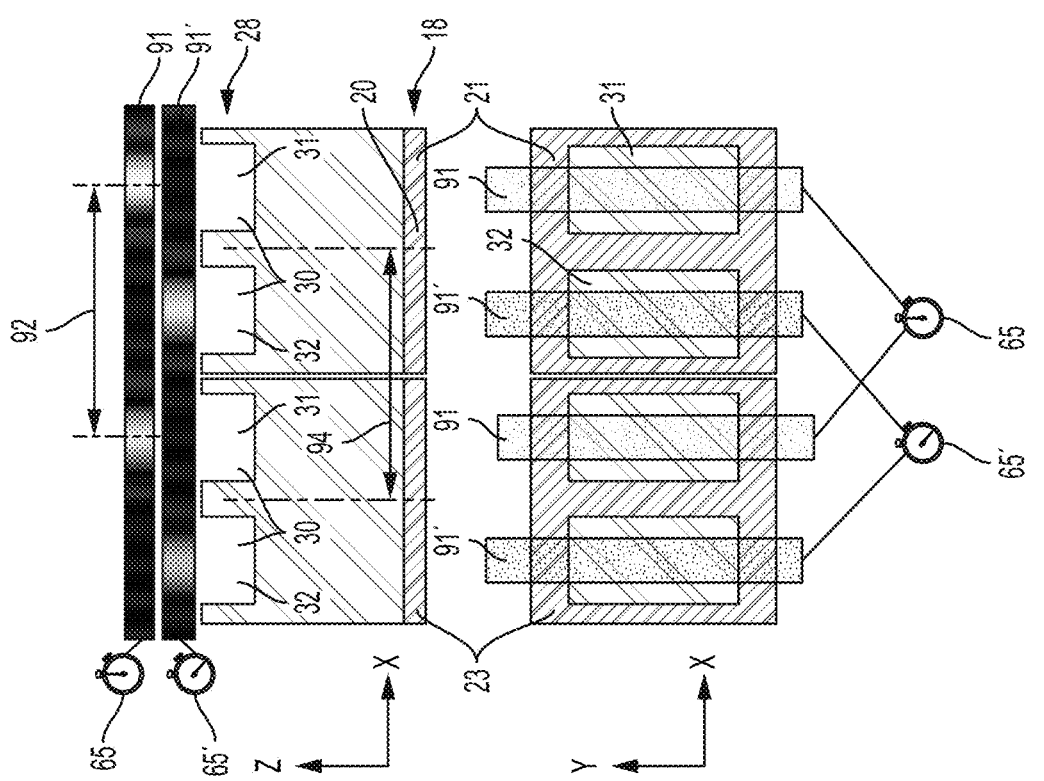
FIG. 9B
FIG. 9A

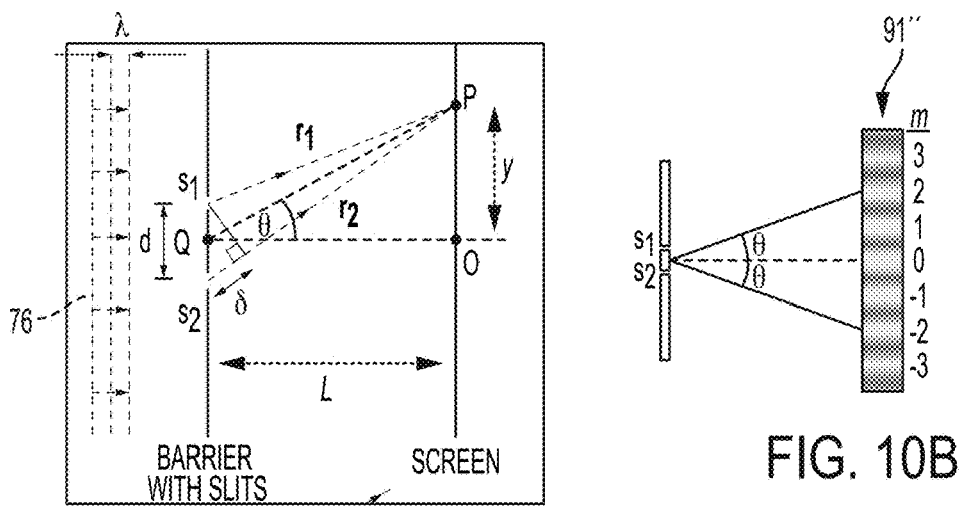
FIG. 10A
FIG. 10B
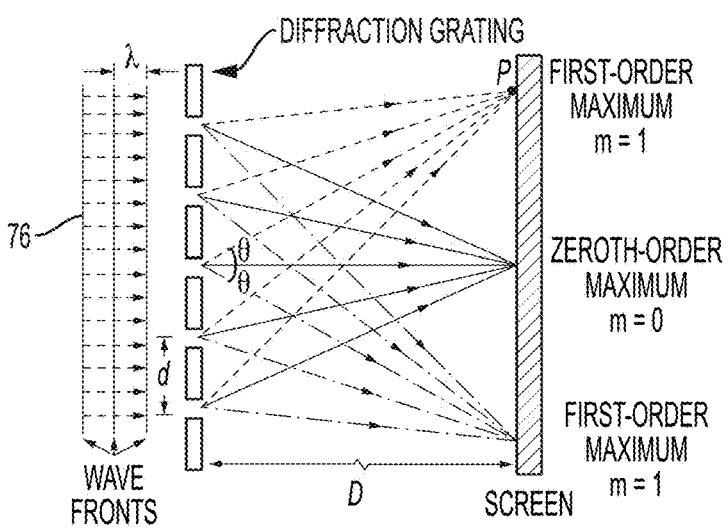
FIG. 11
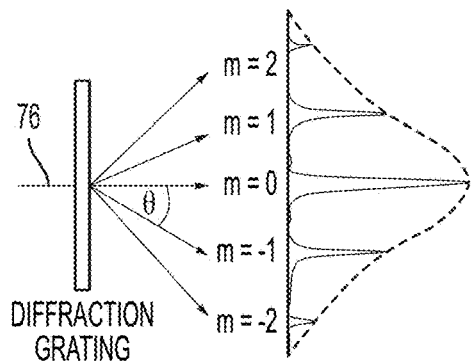
FIG. 12

THE ILLUMINATION PATTERN GENERATOR INCLUDES A MASK LAYER AND THE ILLUMINATION PATTERN GENERATOR ACTUATOR COMPRISES A MASK LAYER ACTUATOR CONNECTED TO THE MASK LAYER TO TRANSLATE OR ROTATE THE MASK LAYER RELATIVE TO THE FORMATION OF FEATURES; A FIRST POSITION OF THE MASK LAYER CAUSES THE PORTION OF THE FIRST PHOTONS TO SELECTIVELY ILLUMINATE THE FIRST FEATURE; A SECOND POSITION OF THE MASK LAYER CAUSES THE PORTION OF THE SECOND PHOTONS TO SELECTIVELY ILLUMINATE THE SECOND FEATURE; THE MASK LAYER INCLUDES A GRATE OF ALTERNATING, PERIODICALLY-SPACED, LIGHT-TRANSMITTING REGIONS AND OPAQUE REGIONS; THE LIGHT-TRANSMITTING REGIONS ARE DEFINED BY PARALLEL STRIPES OF A MASK ABSORBER DISPOSED ON A MASK SUBSTRATE; AND THE PORTION OF THE FIRST PHOTONS AND THE PORTION OF THE SECOND PHOTONS ARE TRANSMITTED THROUGH THE LIGHT-TRANSMITTING REGIONS TO ILLUMINATE PARALLEL ILLUMINATION STRIPES ON THE FORMATION OF FEATURES ~160

FIG. 18B

THE ILLUMINATION PATTERN GENERATOR COMPRISES: AN INTERFERENCE PATTERN GENERATOR TO PROPAGATE LIGHT DEFINING A MULTI-BEAM INTERFERENCE PATTERN ON THE FORMATION OF FEATURES; WHEREIN THE ILLUMINATION PATTERN GENERATOR COMPRISES AN INTERFERENCE PATTERN GENERATOR ACTUATOR CONNECTED TO THE INTERFERENCE PATTERN GENERATOR TO CHANGE A POSITIONAL STATE OR ROTATIONAL STATE OF THE INTERFERENCE PATTERN GENERATOR TO CAUSE THE INTERFERENCE PATTERN TO TRANSLATE OR ROTATE RELATIVE TO THE FORMATION OF FEATURES ~170

FIG. 18C

DEVICE FOR LUMINESCENT IMAGING

CROSS-REFERENCE TO RELATED APPLICATION

This application claims the benefit of U.S. Provisional Application Ser. No. 62/684,907, filed Jun. 14, 2018, and Netherlands Application Serial Number N2021258, filed Jul. 5, 2018; the contents of each of which is incorporated by reference herein in its entirety.

BACKGROUND

Certain sequencing tools rely on various "sequencing by synthesis" (SBS) chemistries to determine a polynucleotide sequence, such as a DNA or RNA sequence. Sequencing can involve using luminescent imaging, such as a fluorescent microscopy system, to identify nucleotides or localized clusters of identical nucleotides by emission wavelength of their respective fluorescent markers. Although some SBS chemistries under development may use a single dye, multiple fluorescent dyes (up to four) are generally used in commercial systems so as to uniquely identify the nucleotides in a polynucleotide, such as A, G, C, and T nucleotides in DNA.

SUMMARY

In a first aspect, a device, comprises a plurality of imaging pixels arranged in a spatial pattern; a formation of features disposed over the plurality of imaging pixels; a first feature of the formation of features, the first feature disposed over a first pixel of the plurality of imaging pixels, a second feature of the formation of features, the second feature disposed over the first pixel and spatially displaced from the first feature; a first luminophore disposed within or over the first feature; a second luminophore disposed within or over the second feature; and a structured illumination source to direct at least a portion of first photons in an illumination pattern to the first feature at a first time, and to direct at least a portion of second photons in the illumination pattern to the second feature at a second time, the second time being different from the first time, the first pixel to selectively receive luminescence emitted by the first luminophore responsive to the portion of the first photons at the first time, and to selectively receive luminescence emitted by the second luminophore responsive to the portion of the second photons at the second time, wherein the structured illumination source includes an illumination pattern generator having an illumination pattern generator actuator connected to the illumination pattern generator to cause the illumination pattern to translate or rotate relative to the formation of features.

In one example of the first aspect, the illumination pattern has illumination intensity maxima with a periodicity corresponding to a pixel spacing in the spatial pattern of the plurality of imaging pixels generator.

In a further example of the one example of the first aspect, the structured illumination source is to flood illuminate the illumination pattern generator with the first photons and the second photons.

In yet another example of the further example of the one example of the first aspect, the structured illumination source comprises a laser.

In a second example of the first aspect, the illumination pattern generator includes a mask layer and the illumination pattern generator actuator comprises a mask layer actuator connected to the mask layer to translate or rotate the mask layer relative to the formation of features.

In an example of the second example of the first aspect, a first position of the mask layer causes the portion of the first photons to selectively illuminate the first feature; and a second position of the mask layer causes the portion of the second photons to selectively illuminate the second feature.

In a further example of the second example of the first aspect, the mask layer includes a grate of alternating, periodically-spaced, light-transmitting regions and opaque regions; the light-transmitting regions are defined by parallel strips of a mask absorber disposed on a mask substrate; and the portion of the first photons and the portion of the second photons are transmitted through the light-transmitting regions to illuminate parallel illumination stripes on the formation of features.

In yet another example of the second example of the first aspect the mask layer includes a two-dimensional arrangement of periodically-spaced, light-transmitting regions defined on an opaque field region; the opaque field region is defined by a mask absorber disposed on a mask substrate; the light-transmitting regions are zones of the mask substrate defined in the opaque field region, the zones having the mask absorber excluded from being disposed thereon; and the portion of the first photons and the portion of the second photons are transmitted through the light-transmitting regions to illuminate corresponding features on the formation of features.

In a third example of the first aspect, the illumination pattern generator comprises: an interference pattern generator to propagate light defining a multi-beam interference pattern on the formation of features; wherein the illumination pattern generator actuator comprises an interference pattern generator actuator connected to the interference pattern generator to change a positional state or rotational state of the interference pattern generator to cause the interference pattern to translate or rotate relative to the formation of features.

In an example of the third example of the first aspect, a first positional state or rotational state of the interference pattern generator causes the portion of the first photons to selectively illuminate the first feature; and a second positional state or rotational state of the interference pattern generator causes the portion of the second photons to selectively illuminate the second feature.

In a further example of the third example of the first aspect, the multi-beam interference pattern is a two-beam interference pattern; the interference pattern generator is to project parallel linear interference fringes on the formation of features; and the parallel linear interference fringes have a predetermined periodicity equal to a pixel spacing.

In another example of the third example of the first aspect, the multi-beam interference pattern is an interference pattern from at least four interfering beams; and the interference pattern is a two-dimensional interference pattern having interference maxima with a predetermined periodicity equal to a pixel spacing.

In a still further example of the third example of the first aspect, the interference pattern generator includes a two-dimensional transmission phase mask to split a laser beam into a set of interfering beams.

In a fourth example of the first aspect, the structured illumination source comprises an optical component, and the device further comprises a controller coupled to the optical component to control the optical component so as to direct the portion of the first photons in the illumination pattern to the first feature at the first time and to direct the portion of the second photons in the illumination pattern to the second feature at the second time.

In an example of the fourth example of the first aspect, the optical component comprises a beam steering component.

In a fifth example of the first aspect, the second feature is laterally displaced from the first feature.

In a sixth example of the first aspect, the device further comprises: a third feature of the formation of features disposed over the first pixel and spatially displaced from each of the first features and second features; a third luminophore disposed within or over the third feature; the structured illumination source to direct at least a portion of third photons to the third feature at a third time, the third time being different from the first time and second time; and the first pixel to selectively receive luminescence emitted by the third luminophore responsive to the portion of the third photons at the third time.

In an example of the sixth example of the first aspect, the device further comprises: a fourth feature of the formation of features disposed over the first pixel and spatially displaced from each of the first features, second features, and third features; a fourth luminophore disposed within or over the fourth feature; the structured illumination source to direct at least a portion of fourth photons to the fourth feature at a fourth time, the fourth time being different from the first time, second time, and third time; and the first pixel to selectively receive luminescence emitted by the fourth luminophore responsive to the portion of the fourth photons at the fourth time.

In a seventh example of the first aspect, the first and second photons have wavelengths in a range from about 300 nm to about 800 nm.

It is to be understood that any elements of this first aspect of the device may be combined together in any desirable manner and/or configuration.

In a second aspect, a method comprises: directing, by a structured illumination source, at least a portion of first photons in an illumination pattern to a first feature at a first time, wherein the first feature is a member of a formation of features disposed over a plurality of imaging pixels arranged in a spatial pattern in a luminescent imaging device, and wherein the first feature of the formation of features is disposed over a first pixel of the plurality of imaging pixels; directing, by the structured illumination source, at least a portion of second photons in the illumination pattern to a second feature at a second time, the second time being different from the first time, wherein the second feature is a member of the formation of features, and wherein the second feature of the formation of features is disposed over the first pixel and spatially displaced from the first feature; selectively receiving, by the first pixel, luminescence emitted by a first luminophore responsive to the portion of the first photons at the first time, wherein the first luminophore is disposed within or over the first feature; and selectively receiving, by the first pixel, luminescence emitted by a second luminophore responsive to the portion of the second photons at the second time, wherein the second luminophore is disposed within or over the second feature, wherein the structured illumination source includes an illumination pattern generator having an illumination pattern generator actuator connected to the illumination pattern generator to cause the illumination pattern to translate or rotate relative to the formation of features.

In a first example of this second aspect, the illumination pattern has illumination intensity maxima with a periodicity corresponding to a pixel spacing in the spatial pattern of the plurality of imaging pixels.

In another example of the first example of this second aspect, the illumination pattern generator includes a mask layer and the illumination pattern generator actuator comprises a mask layer actuator connected to the mask layer to translate or rotate the mask layer relative to the formation of features; a first position of the mask layer causes the portion of the first photons to selectively illuminate the first feature; a second position of the mask layer causes the portion of the second photons to selectively illuminate the second feature; the mask layer includes a grate of alternating, periodically-spaced, light-transmitting regions and opaque regions; the light-transmitting regions are defined by parallel strips of a mask absorber disposed on a mask substrate; and the portion of the first photons and the portion of the second photons are transmitted through the light-transmitting regions to illuminate parallel illumination stripes on the formation of features.

In yet another example of the first example of this second aspect, the illumination pattern generator comprises: an interference pattern generator to propagate light defining a multi-beam interference pattern on the formation of features; wherein the illumination pattern generator actuator comprises an interference pattern generator actuator connected to the interference pattern generator to change a positional state or rotational state of the interference pattern generator to cause the interference pattern to translate or rotate relative to the formation of features.

It is to be understood that any elements of this second aspect of the method may be combined together in any desirable manner and/or configuration.

In a third aspect, a device comprises: a plurality of imaging pixels arranged in a spatial pattern; a formation of features disposed over the plurality of imaging pixels; an illumination pattern generator; a first feature of the formation of features, the first feature being disposed over a first pixel of the plurality of imaging pixels; and a second feature of the formation of features, the second feature disposed over the first pixel and spatially displaced from the first feature; wherein the illumination pattern generator includes an illumination pattern generator actuator connected to the illumination pattern generator to cause an illumination pattern having illumination intensity maxima with a periodicity corresponding to a pixel spacing in the spatial pattern of the plurality of imaging pixels to selectively irradiate the first feature with light at a first time; and wherein the illumination pattern generator is tuned to selectively irradiate the second feature with light at a second time, the second time being different from the first time.

In a first example of this third aspect, the device further comprises: a structured illumination source to generate first photons at the first time, and to generate second photons at the second time; a first luminophore disposed within or over the first feature and a second luminophore disposed within or over the second feature; a first target analyte disposed within or over the first feature and a second target analyte disposed within or over the second feature, wherein the first target analyte is different from the second target analyte; and the first target analyte and second target analyte comprise nucleic acids having different sequences.

In a second example of this third aspect, the illumination pattern generator is disposed over the formation of features.

It is to be understood that any elements of the third aspect of the device may be combined together in any desirable manner. Moreover, it is to be understood that any combination of elements of the third aspect of the device and/or of the second aspect of the method and/or of the first aspect of the device may be used together, and/or that any elements from any one or more of these aspects may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 9A and FIG. 9B are schematic diagrams depicting the selectivity of multi-beam interference patterns in examples of the present disclosure;

FIG. 10A is a schematic diagram illustrating certain geometry and terminology relating to interference;

FIG. 10B is a simplified version of FIG. 10A that also includes a depiction of the interference fringes;

FIG. 11 is a schematic diagram that applies the interference relationships of the "double-slit" demonstration of FIG. 10A to a diffraction grating having a many slits;

FIG. 12 is a schematic diagram that depicts the relative intensity of orders m produced by a coherent beam of light 76 diffracted by a diffraction grating;

FIGS. 18A-18C together are a flow diagram depicting an example of a method according to the present disclosure.

DETAILED DESCRIPTION

Figure 1A:
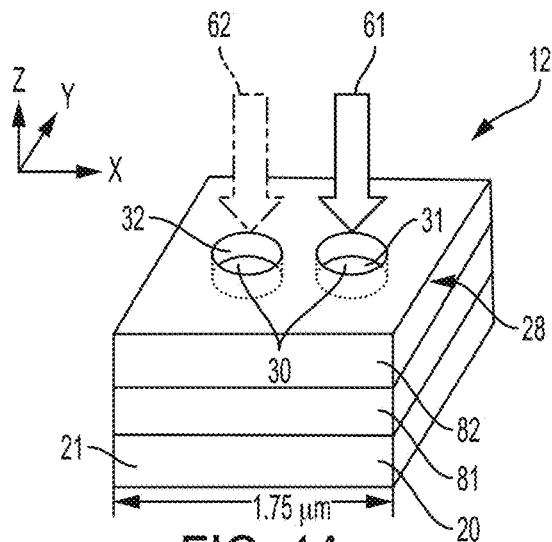
FIG. 1A is a schematic perspective view of an example of portion of a device according to the present disclosure.

Examples of the present disclosure include devices for luminescent imaging and methods of using the same.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

As used herein, the term "well" means a discrete concave feature in a material having a surface opening (aperture) that is completely surrounded by interstitial region(s) of the surface. A well can have characteristics such as size (e.g., volume, diameter, and depth), cross-sectional shape (e.g., round, elliptical, triangular, square, polygonal, star shaped (having any suitable number of vertices), irregular, or having concentric wells separated by a dielectric material), and distribution (e.g., spatial locations of the wells within the dielectric material, e.g., regularly spaced or periodic locations, or irregularly spaced or aperiodic locations). The cross section of a well can be, but need not necessarily be, uniform along the length of the well.

As used herein, the term "post" means a discrete convex feature protruding from the surface of a material and that is completely surrounded by interstitial region(s) of the surface. A post can have characteristics such as size (e.g., volume, diameter, and depth), shape (e.g., round, elliptical, triangular, square, polygonal, star shaped (having any suitable number of vertices), irregular, or having concentric posts separated by a dielectric material), and distribution (e.g., spatial locations of the posts protruding from the surface of the dielectric material, e.g., regularly spaced or periodic locations, or irregularly spaced or aperiodic locations). The cross section of a post can be, but need not necessarily be, uniform along the length of the post.

As used herein, the term "surface" means a part or layer of a material that is in contact with another material.

As used herein, the term "interstitial region" is intended to mean an area in a material or on a surface that separates areas of the material or surface. For example, an interstitial region can separate one feature of a formation of features from another feature of the formation of features, or an interstitial region can separate one site of a matrix from another site of the matrix.

As used herein, the term "luminescent" means emitting cold body radiation, and the term "luminophore" means an item that is luminescent. The term "luminescent" is intended to be distinct from incandescence which is radiation emitted from a material as a result of heat.

Generally luminescence results when an energy source displaces an electron of an atom out of its lowest energy ground state into a higher energy excited state; then the electron returns the energy in the form of radiation so it can fall back to its ground state. A type of luminescent item is one that emits cold body radiation when energy is provided by excitation radiation. Such items can be referred to as "photoluminescent." Examples of photoluminescent items include "fluorescent" items that emit cold body radiation relatively quickly (e.g., less than a millisecond) after excitation radiation, and "phosphorescent" items that emit cold body radiation relatively slowly (e.g., greater than or equal to a millisecond) after excitation radiation. Photoluminescence can be perceived or received as emission of radiation by an item at a wavelength that is a result of irradiating the item at another wavelength. Another type of luminescent item is one that emits cold body radiation when energy is provided by a chemical or biological reaction. Such items can be referred to as "chemiluminescent."

Any of a variety of signals can be detected in a device and/or method set forth herein including, for example, an optical signal such as absorbance of radiation, luminescence emission, luminescence lifetime, luminescence polarization, or the like; Rayleigh and/or Mie scattering; or the like.

Examples of labels that can be detected in a method set forth herein include, without limitation, a fluorophore, luminophore, chromophore, nanoparticle (e.g., gold, silver, carbon nanotubes), or the like.

As used herein the term "feature" means a distinctive variation in the structure or composition of a material such as a solid support. Optionally, the variation is also repeated in the structure or composition of the material. A collection of the features can form a matrix or lattice in or on the material. Examples of features include, but are not limited to wells, posts, ridges, channels, sites bearing analytes, layers of a multilayer material, areas in or on a material having a chemical composition that differ from the chemical composition of other areas in or on the material and the like. A feature can have characteristics such as size (e.g., volume, diameter, and depth), shape (e.g., round, elliptical, triangular, square, polygonal, star shaped (having any suitable number of vertices), irregular, or having concentric features separated by a dielectric material), and distribution (e.g., spatial locations of the features within the dielectric material, e.g., regularly spaced or periodic locations, or irregularly spaced or aperiodic locations). The cross section of a feature can be, but need not necessarily be, uniform along the length of the feature.

As used herein, the term "site" means a location in a matrix for a particular species of molecule or cell (or other analyte). A site can contain only a single molecule (or cell or other analyte) or it can contain a population of several molecules (or cells or analytes) of the same species. In some examples, sites are present on a material prior to attaching a particular analyte. In other examples, the site is created by attachment of a molecule or cell (or other analyte) to the material. Sites of a matrix may be discrete. The discrete sites can be contiguous or they can have spaces between each other. It will be understood that a site is a type of feature. A feature can function as a component of a formation of features.

As used herein, the term "formation" means a population of features that can be differentiated from each other according to relative location.

As used herein, the term "pitch," when used in reference to features of a formation, or elements of a spatial pattern, is intended to refer to the center-to-center spacing for adjacent features of the formation or elements of the spatial pattern. A periodic characteristic of a formation of features can be characterized in terms of average pitch. The formation can be ordered such that the coefficient of variation around the average pitch is small. The average pitch can be, for example, at least about on the order of a wavelength of light in one or more regions of the spectrum. For example, the pitch can correspond to wavelengths in one or more of the visible spectrum (about 380-700 nm), ultraviolet (UV) spectrum (less than about 380 nm to about 10 nm) and IR spectrum (greater than about 700 nm to about 1 mm). A formation of features can have different pitches in different directions.

The spacing between features of the same type or a different type respective to another type can be ordered, for example, forming a regular, repeating structure such as a rectilinear grid or a hexagonal grid.

As used herein, the term "nucleotide" or "nucleic acid" is intended to mean a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), deoxyuridine triphosphate (dUTP), reversibly blocked adenosine triphosphate (rbATP), reversibly blocked thymidine triphosphate (rbTTP), reversibly blocked cytidine triphosphate (rbCTP), and reversibly blocked guanosine triphosphate (rbGTP). For further details on reversibly blocked nucleotide triphosphates (rbNTPs), see U.S. Patent Publication No. 2013/0079232, the entire contents of which are incorporated by reference herein.

The term "nucleotide" or "nucleic acid" also is intended to encompass any nucleotide analogue which is a type of nucleotide that includes a modified nucleobase, sugar and/or phosphate moiety. Example modified nucleobases that can be included in a polynucleotide, whether having a native backbone or analogue structure, include, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "polynucleotide" refers to a molecule that includes a sequence of nucleotides that are bonded to one another. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA, or can include a mixture of a single stranded and double stranded sequences of nucleotides. Double stranded DNA (dsDNA) includes genomic DNA, and polymerase chain reaction (PCR) and amplification products. Single stranded DNA (ssDNA) can be converted to dsDNA and vice-versa. The precise sequence of nucleotides in a polynucleotide can be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, eDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, "chemically coupled" is intended to mean an attachment between a first member and a second member. In some examples, such an attachment may be irreversible under the conditions in which the attached members are used. In other examples, such an attachment may be reversible but persistent for at least the period of time in which it is used for one or more steps of an analytical or preparative technique set forth herein (e.g. an analytical step of detecting a subunit of a polymer). Such attachment can be formed via a chemical bond, e.g., via a covalent bond, hydrogen bond, ionic bond, dipole-dipole bond, London dispersion forces, or any suitable combination thereof. Covalent bonds are one example of an attachment that suitably can be used to couple a first member to a second member. Other examples include duplexes between oligonucleotides, peptide-peptide interactions, and hapten-antibody interactions such as streptavidin-biotin, streptavidin-desthiobiotin, and digoxigenin-anti-digoxigenin. In one embodiment, an attachment can be formed by hybridizing a first polynucleotide to a second polynucleotide that inhibits detachment of the first polynucleotide from the second polynucleotide. Alternatively, an attachment can be formed using physical or biological interactions, e.g., an interaction between a first protein and a second protein that inhibits detachment of the first protein from the second protein.

As used herein, a "polymerase" is intended to mean an enzyme having an active site that assembles polynucleotides by polymerizing nucleotides into polynucleotides. A polymerase can bind a primed single stranded polynucleotide template, and can sequentially add nucleotides to the growing primer to form a polynucleotide having a sequence that is complementary to that of the template.

In examples of the device of the present disclosure, monolithic integration of microfluidic chips on top of CMOS imaging arrays can be used to reduce the size of, e.g., miniaturize, DNA sequencers. Throughput of CMOS-based sequencing devices can be limited by the size of imaging pixels. For example, relatively large pixel sizes can be useful for providing sufficient signal collection from individual DNA molecules or clusters of identical molecules. Although pixels can be made smaller so as to increase throughput, such size reduction can reduce full well capacity and can increase cross-talk between pixels, thereby reducing the signal-to-noise ratio (SNR) of the imaging, and the sequencing. Such an approach also can increase the cost of fabricating the imaging matrix, e.g., by increasing the amount of engineering of the imaging matrix as well as the integration of such imaging matrix with microfluidic components.

An alternative way of increasing throughout by providing more testing sites per device can involve introducing multiple luminescence sites (e.g., DNA clusters, microarray reaction chambers, or the like) per pixel. For example, some examples of the present disclosures can image multiple sites, each of which can include a respective analyte, using an imaging pixel by selectively exciting different sites at different times than one another using a structured illumination source, and obtaining a respective image at each such time. Illustratively, a plurality of imaging pixels can be provided, and multiple sites can be disposed over each such imaging pixel. Relative to a sequencing device in which only one site is disposed over each given pixel, the present multi-site per pixel configuration can significantly increase the number of sites that can be imaged using a given plurality of imaging pixels. However, if all of the sites disposed over a given imaging pixel were to be excited simultaneously with one another, the imaging pixel would receive luminescence from each such site simultaneously with one another, thus impeding the ability to distinguish between luminescence from one such site and luminescence from another such site based on an electrical signal that the pixel generates responsive to receiving such luminescence.

A structured illumination source such as disclosed herein can be used so as selectively to excite a single one of the multiple sites disposed over a given imaging pixel at a given time, so as to obtain an electrical signal from that pixel responsive to luminescence just from that site at that time, and subsequently to excite a second one of the multiple sites over that imaging pixel at a second time, so as to obtain a second electrical signal from that pixel responsive to luminescence from that second site. As such, the luminescence from the two sites can be distinguished from one another based on the electrical signals obtained from the imaging pixel at the two times. As such, examples of the devices and methods of the present disclosure can provide luminescent imaging of a greater number of sites than the number of pixels in a plurality of imaging pixels, e.g., an integer multiple n of the number of pixels, where n is greater than or equal to 2, or 3, or 4, or 5, or greater than 5.

As provided herein, the different sites disposed over an imaging pixel can be selectively excited by selectively directing excitation photons to respective ones of the sites at different times than one another. As another example, the sites can be irradiated at a first time with any suitable number of laser beams that interfere with one another in such a manner as to generate a first optical intensity pattern that selectively excites one of the sites per imaging pixel at the first time, and can be irradiated at a second time with any suitable number of laser beams that interfere with one another in such a manner as to generate a second optical intensity pattern that selectively excites another one of the sites per imaging pixel at the second time. The pixel can generate respective electrical signals at the first and second times responsive to luminescence from the respective sites.

FIG. 1A schematically illustrates a perspective view of an example of a portion 12 of a device 10 for use in luminescent imaging of a plurality of sites 25 within an imaging pixel 20. The portion 12 of the device 10 illustrated in FIG. 1A includes an imaging pixel 20, such as a complementary metal oxide semiconductor (CMOS) based image sensor; a stacked layer 81 disposed over the imaging pixel 20; and a plurality of features 30 (in FIG. 1A, the features 30 are two nanowells) defined within a feature layer 82 disposed over the stacked layer 81. The stacked layer 81, though shown as a single layer, may represent a plurality of layers, for example, silicon layer(s), dielectric layer(s), metal layer(s), etc. The stacked layers may make up device circuitry, which includes detection circuitry. The stacked layers 81 may include optical components such as optical waveguide(s), filter(s), etc. A site 25 (see, e.g., FIG. 2A) including one or more luminophores 40, e.g., one or more analytes respectively coupled to luminophores 40, e.g., one or more nucleotides respectively coupled to luminophores 40, can be disposed within each nanowell. The luminophore(s) 40 can be disposed in the nanowell and excited evanescently by the excitation wavelengths, e.g., photons having suitable wavelengths (illustrated as first photons 61 and second photons 62 in FIG. 1A). The arrow representing second photons 62 is shown in phantom line in FIG. 1A because the first photons 61 and the second photons 62 are emitted at different times. The imaging pixel 20 can be suitably electronically coupled to a detection circuit (not specifically illustrated), which can be configured so as to receive and analyze an electrical signal generated by the imaging pixel 20 responsive to luminescence generated by the luminophore(s). The imaging pixel 20 in FIG. 1A may have a dimension of 1.75 μm on each side; however it should be appreciated that imaging pixels 20 of any suitable dimensions can be used.

Figure 1B:
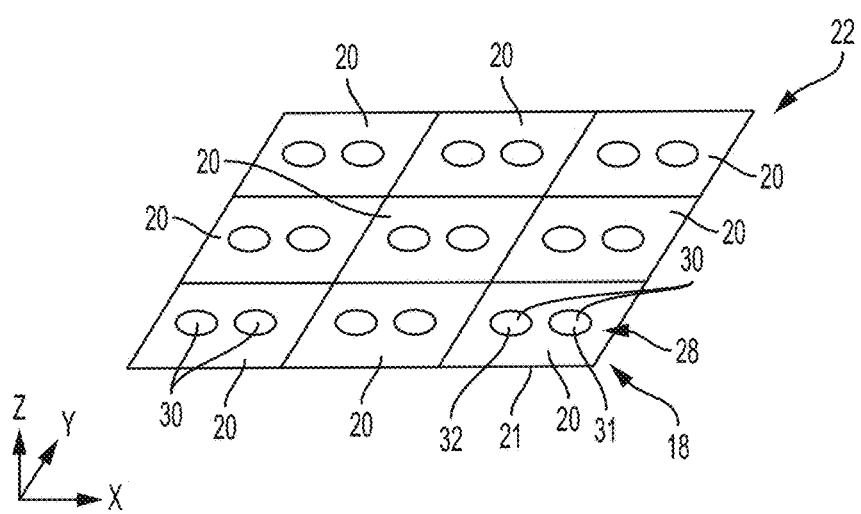
FIG. 1B is a schematic perspective view of an example of a formation of features according to the present disclosure.
Figure 1C:
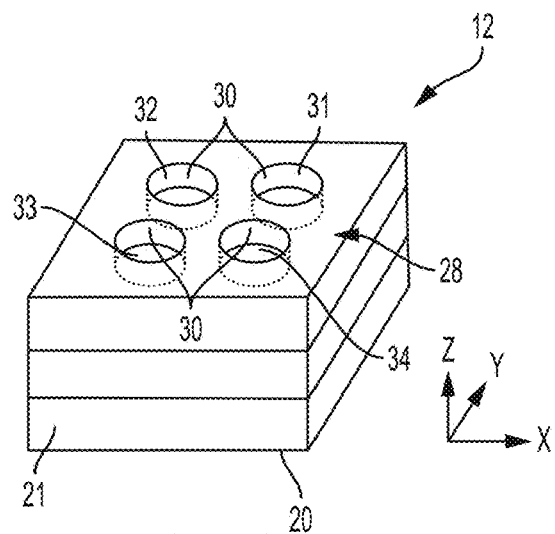
FIG. 1C is a schematic perspective view of an example of a portion of a device that includes a third and a fourth feature of the formation of features according to the present disclosure.

Optionally, a plurality of any suitable number of such portions 12 of the device 10 can be provided, arranged in a spatial pattern. For example, FIG. 1B schematically illustrates a perspective view of an example of a formation 28 of features 30 disposed over a plurality 18 (see FIG. 1C) of the imaging pixels 20 arranged in a spatial pattern 22. In FIG. 1C, the spatial pattern 22 is a matrix having 3 rows and 3 columns in an X-Y plane. In examples of the present disclosure, a plurality of features 30 corresponds to each imaging pixel 20. For example, as depicted in FIG. 1A, a first feature 31 of the formation 28 of features 30 is disposed over a first pixel 21 of the plurality of imaging pixels 20. (It is to be understood that FIG. 1A is only a portion of the device 10 having a plurality 18 of imaging pixels 20 as depicted in FIG. 1B.) A second feature 32 of the formation 28 of features 30 is disposed over the first pixel 21 and spatially displaced from the first feature 31. FIG. 1C depicts an example that includes a third feature 33 and a fourth feature 34 of the formation 28 of features 30 disposed over the first pixel 21 and spatially displaced from each of the other features 30. In examples of the present disclosure, any number of features 30 greater than one may be disposed over each imaging pixel, e.g., 2, 3, 4, 5, 6, 7, 8 or more features may be disposed over each imaging pixel 20. As illustrated in FIGS. 1A-1C, a formation 28 of features 30, e.g., a plurality of nanowells spatially arranged in a pattern that is repeated, can be disposed over each imaging pixel 20. As such, each imaging pixel 20 can receive luminescence from luminophore(s) 40 disposed within the nanowells over that imaging pixel 20, and generate a suitable electronic signal responsive to receipt of such luminescence.

Figure 2A:
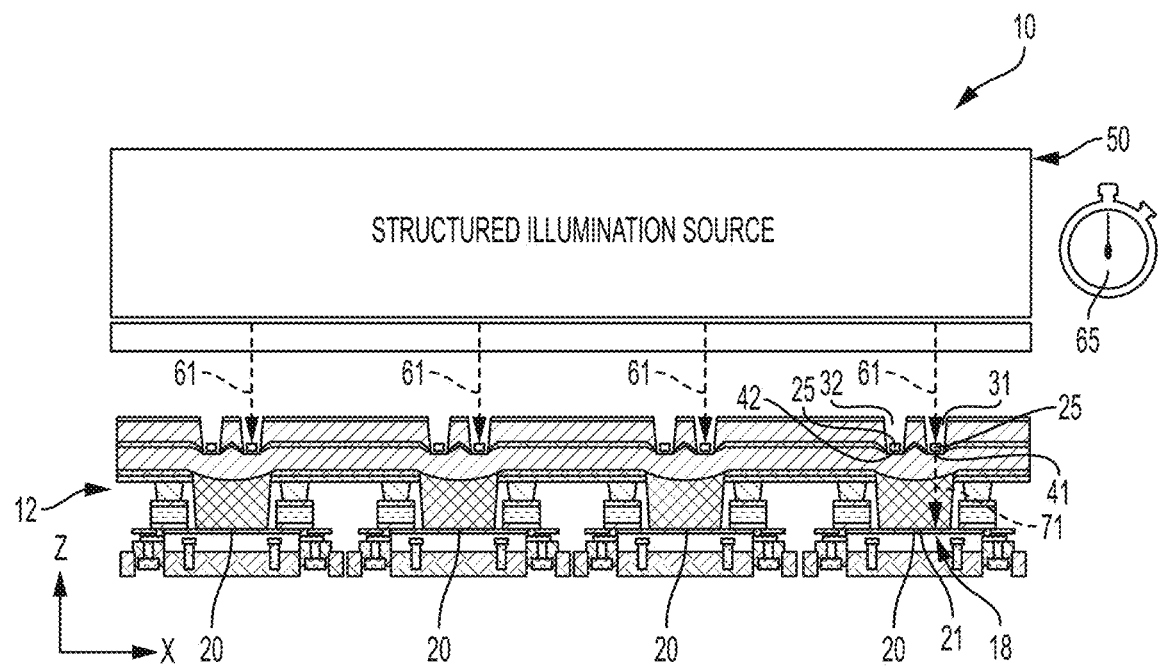
FIG. 2A is a schematic cross-sectional side view of an example of a device according to the present disclosure, including the portion of the device depicted in FIG. 1A depicted at a first time.

FIG. 2A is a schematic cross-sectional side view of an example of a device 10 of the present disclosure, including the portion 12 of the device depicted in FIG. 1A. In FIG. 2A, the example of the device 10 includes a plurality 18 of imaging pixels 20 arranged in a spatial pattern 22. The spatial pattern 22 is best seen in FIG. 1B. A formation 28 of features 30 is disposed over the plurality 18 of imaging pixels 20. A first feature 31 of the formation 28 of features 30 is disposed over a first pixel 21 of the plurality 18 of imaging pixels 20. A second feature 32 of the formation 28 of features 30 is disposed over the first pixel 21 and spatially displaced from the first feature 31. In an example, the second feature 32 is laterally displaced from the first feature 31.

Figure 2B:
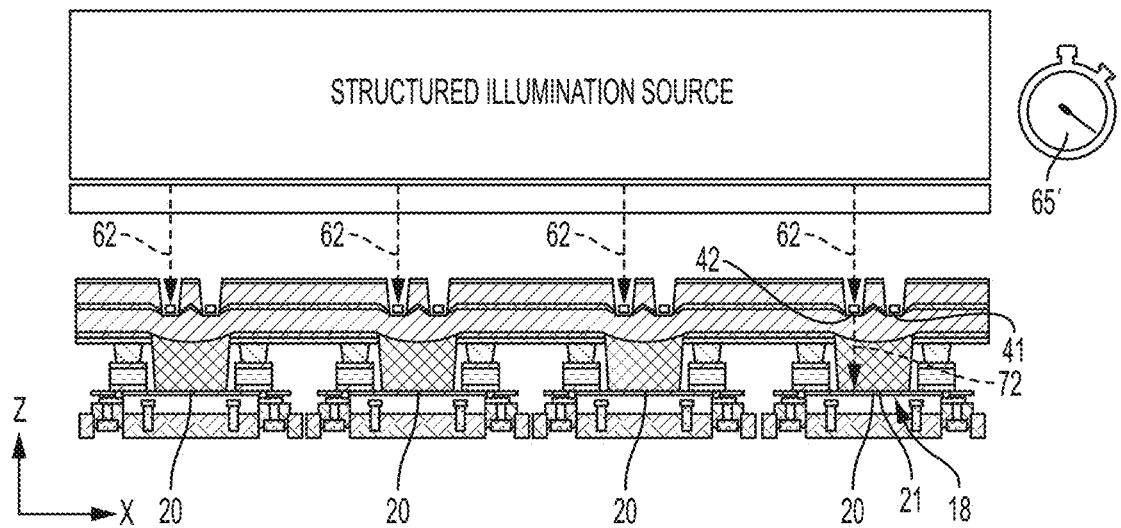
FIG. 2B is a schematic cross-sectional side view of the example of the device depicted in FIG. 2A, depicted at a second time.

Referring again to FIG. 2A, a first luminophore 41 is disposed within or over the first feature 31. (For example, if the first feature 31 is a nanowell, the first luminophore 41 may be disposed within the first feature 31 (nanowell); if the first feature 31 is a post, the first luminophore 41 may be disposed over the first feature 31 (post). A second luminophore 42 is disposed within or over the second feature 32. A structured illumination source 50 is to direct at least a portion of first photons 61 in an illumination pattern to the first feature 31 at a first time. The first time is schematically indicated in FIG. 2A by watch face 65. The structured illumination source 50 is to direct at least a portion of second photons 62 in the illumination pattern to the second feature 32 at a second time, the second time being different from the first time. The second time is indicated by watch face 65'. The first pixel 21 is to selectively receive luminescence 71 emitted by the first luminophore 41 responsive to the first photons 61 at the first time (FIG. 2A), and to selectively receive luminescence 72 emitted by the second luminophore 42 responsive to the second photons 62 at the second time (FIG. 2B). The structured illumination source 50 includes an illumination pattern generator 52 having an illumination pattern generator actuator connected to the illumination pattern generator 52 to cause the illumination pattern to translate or rotate relative to the formation 28 of features 30. In examples, the illumination pattern generator actuator may be any actuator that is connected to the illumination pattern generator 52 to cause the illumination pattern to translate or rotate relative to the formation 28 of features 30. It is to be understood that the illumination pattern generator actuator moves the illumination pattern at the same time, by the action of the illumination pattern generator actuator. For example, the illumination pattern generator actuator may be a mask layer actuator 55 to actuate a mask layer 53. In another example, an interference pattern generator actuator 95 connected to an interference pattern generator 93 to change a positional state of the interference pattern generator 93 to cause the interference pattern to translate or rotate relative to the formation 28 of features 30. In yet another example, a controller 47 is coupled to an optical component 46 to control the optical component 46 so as to translate or rotate the illumination pattern. Thus, the controller 47 (i.e., an actuator) may rotate a mirror (i.e., an optical component) to move an entire illumination pattern to illuminate all of the features 30 that have a position relative to the individual pixels that corresponds to the first feature 31 at a first time, and a second feature 32 at a second time.

As provided herein, the quantity of features 30 can be increased as an integer multiple n>1 of the quantity of imaging pixels 20 by selectively exciting different ones of such features 30 at different times than one another. For example, FIG. 1B schematically illustrates a perspective view of an example of a formation 28 of features 30 such as provided herein, wherein multiple features 30 correspond to each imaging pixel 20. The formation 28 of features 30 has the features 30 repeating in the same spatial pattern 22 in which the plurality 18 of imaging pixels 20 is arranged. In the non-limiting example illustrated in FIG. 1C, four features 30 (respectively illustrated as first feature 31, second feature 32, third feature 33, and fourth feature 34) are provided per imaging pixel 20, although it should be appreciated that any suitable number of features 30 can be provided per pixel, e.g., two or more features per pixel, three or more features per pixel, four or more features per pixel, or five or more features per pixel. Such features can be provided using any suitable geometric characteristics. A plurality of features 30, such as a plurality of nanowells, can be defined in the feature layer 82 (see FIG. 1A).

As illustrated in FIGS. 1A-2B, multiple features 30, e.g., multiple nanowells can be disposed over each imaging pixel 20. As such, each imaging pixel 20 can receive luminescence at different times from luminophore(s) 40 disposed within or over each such feature 30, e.g., within each such nanowell, over that imaging pixel 20, and generate a suitable electronic signal responsive to receipt of such luminescence at such different times. The imaging pixel 20, the stacked layer 81, and the features 30 optionally can be monolithically integrated with one another.

In some examples of the present disclosure, the formation 28 of features 30 can include a plurality of wells; the first feature 31 can include a first well within which the first luminophore is disposed, and the second feature 32 can include a second well within which the second luminophore is disposed, e.g., in a manner similar to that illustrated in FIG. 2A. In other examples, the formation 28 of features 30 can include a plurality of posts; the first feature 31 can include a first post upon which the first luminophore is disposed, and the second feature 32 can include a second post upon which the second luminophore is disposed. Illustratively, the first and second features (e.g., wells or posts) each can have a substantially circular cross-section.

Figure 3A:
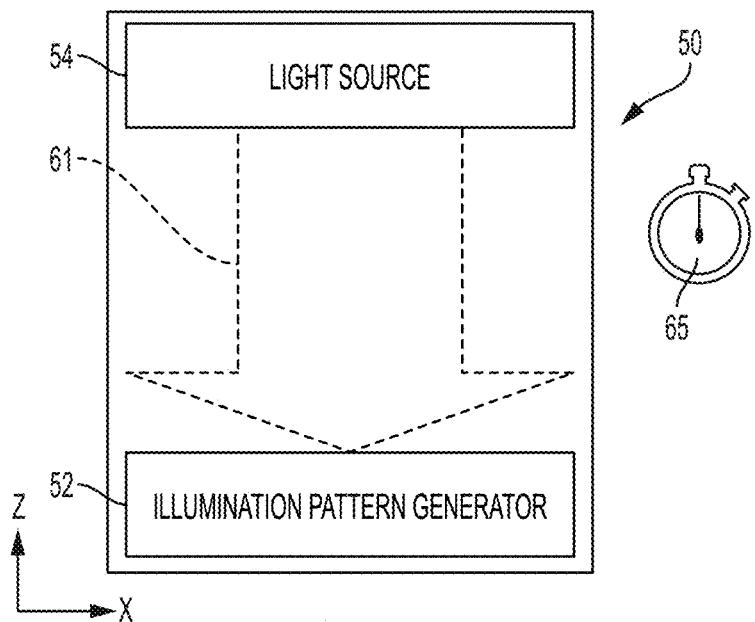
FIG. 3A is a block diagram depicting an example of a structured illumination source at a first time as disclosed herein.
Figure 3B:
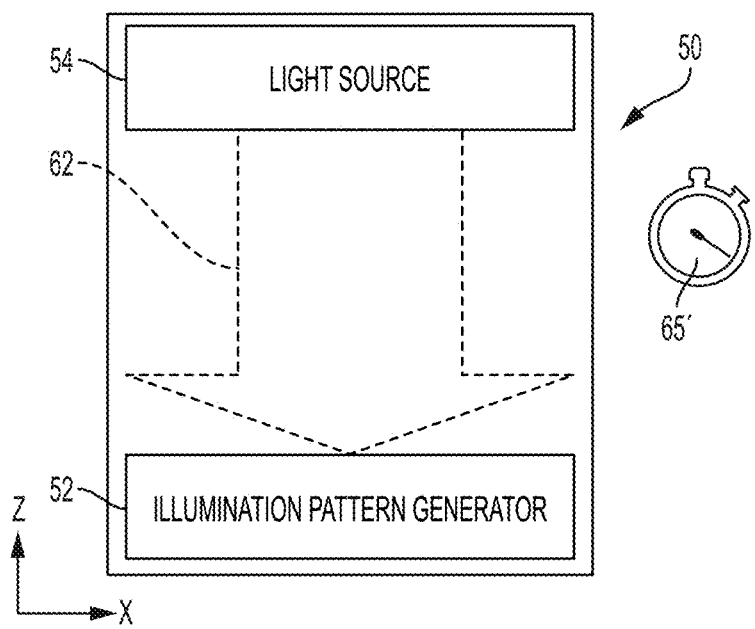
FIG. 3B is a block diagram depicting the example of the structured illumination source shown in FIG. 3A at a second time as disclosed herein.

FIG. 3A and FIG. 3B are block diagrams depicting an example of a structured illumination source 50 as disclosed herein. As illustrated in FIG. 3A and in FIG. 3B, in examples of the present disclosure, the structured illumination source 50 may include an illumination pattern generator 52. The structured illumination source 50 may be to flood illuminate the illumination pattern generator 52 with the first photons 61 (FIG. 3A) and the second photons 62 (FIG. 3B). As used herein, the term "flood illuminate" means that the illumination is provided to a surface all at once rather than scanning a narrow beam over portions of the surface. In examples, the structured illumination source 50 includes a light source 54. The light source 54 may emit white light, monochrome light, or photons with any combination of wavelengths. The light source 54 may be a broadband source of light, such as a light emitting diode (LED) 54' (see, e.g., FIG. 15A), or a narrowband excitation source, such as a laser 54" (see, e.g., FIG. 14) or any other suitable source of photons. Optical components may be included between the light source 54 and the illumination pattern generator 52. For example, optical components may be included to filter white light to a narrow band of frequencies, to polarize, to collimate, and/or to expand a beam emitted by the light source 54. The first and second photons emitted by the light source 54 can be in the optical range of the spectrum, e.g., the first and second photons may have wavelengths in a range from about 300 nm to about 800 nm.

Figure 4A:
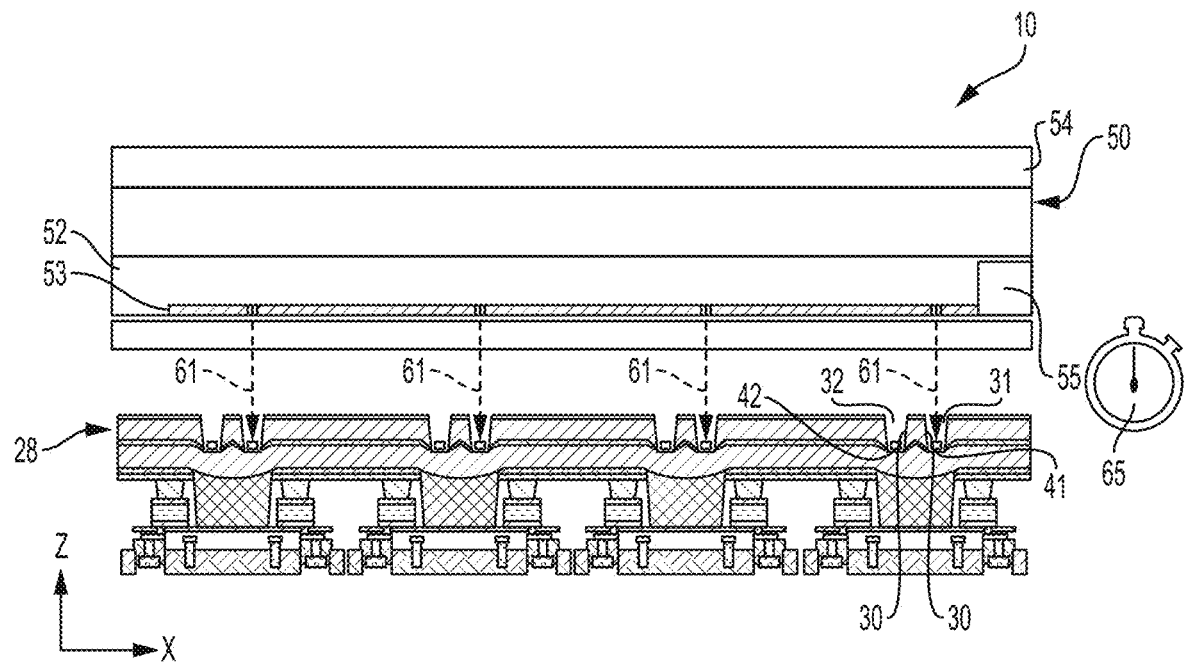
FIG. 4A is a schematic side view of an example of a device shown at a first time according to the present disclosure.
Figure 4B:
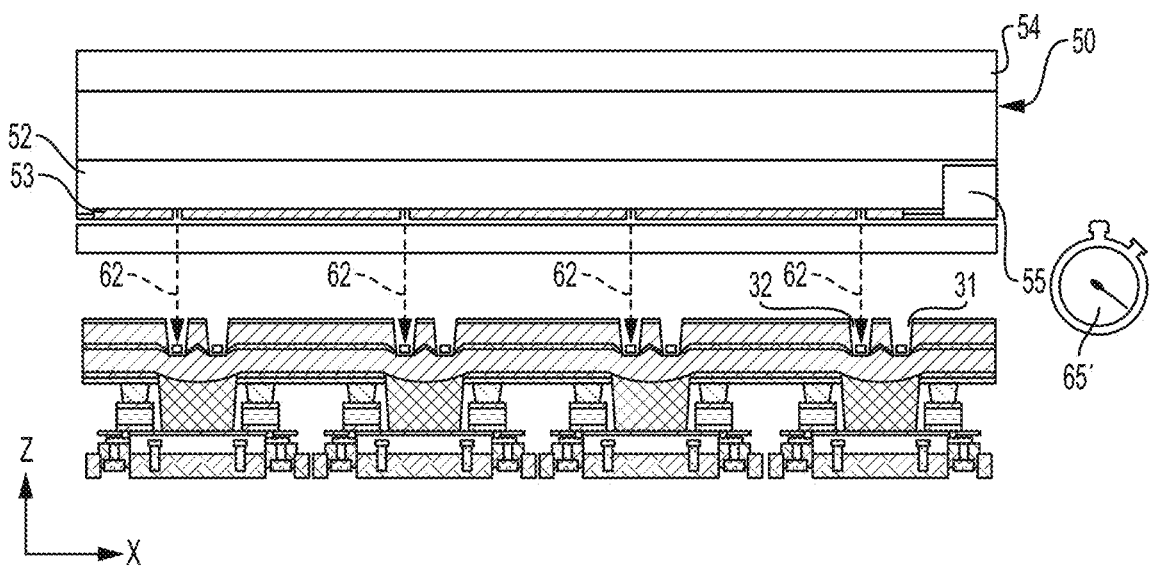
FIG. 4B is a schematic side view of the example of the device shown in FIG. 4A at a second time according to the present disclosure.

FIG. 4A is a schematic side view of an example of a device 10 of the present disclosure. FIG. 4A is similar to FIG. 2A except FIG. 4A depicts schematic details of an example of a structured illumination source 50. As depicted in FIG. 4A, in examples of the device 10, the illumination pattern generator 52 may include a mask layer 53 and the illumination pattern generator actuator includes a mask layer actuator 55 connected to the mask layer 53 to translate or rotate the mask layer 53 relative to the formation 28 of features 30. As depicted in FIG. 4A, a first position of the mask layer 53 causes the portion of the first photons 61 to selectively illuminate the first feature 31. As depicted in FIG. 4B, a second position of the mask layer 53 causes the portion of the second photons 62 to selectively illuminate the second feature 32.

In some examples of the present disclosure, a device 10 includes a plurality 18 of imaging pixels 20 arranged in a spatial pattern 22. A formation 28 of features 30 is disposed over the plurality 18 of imaging pixels 20. In some examples, an illumination pattern generator 52 may be disposed over the formation 28 of features 30. In some examples, the illumination pattern generator 52 may be formed as part of the structure with the formation 28 of features 30. In other examples, the illumination pattern generator 52 may be formed as a structure separate from the formation 28 of features 30. A first feature 31 of the formation 28 of features 30 is disposed over a first pixel 21 of the plurality 18 of imaging pixels 20. A second feature 32 of the formation 28 of features 30 is disposed over the first pixel 21 and spatially displaced from the first feature 31. The illumination pattern generator 52 includes an illumination pattern generator actuator connected to the illumination pattern generator 52 to cause an illumination pattern having illumination intensity maxima with a periodicity 92 corresponding to a pixel spacing 94 in the spatial pattern 22 of the plurality 18 of imaging pixels 20 to selectively irradiate the first feature 31 with light at a first time. The illumination pattern generator 52 causes the illumination pattern to selectively irradiate the second feature 32 with light at a second time, the second time being different from the first time. In examples, the illumination intensity maxima may be interference maxima 73, or other locations of illumination intensity such as illumination stripes 67 (e.g., FIG. 5B) or spots (e.g., FIG. 6B).

The device 10 may further include a structured illumination source 50 to generate first photons 61 at the first time, and to generate second photons 62 at the second time. A first luminophore 41 may be disposed within or over the first feature 31 and a second luminophore 42 may be disposed within or over the second feature 32. A first target analyte may be disposed within or over the first feature 31 and a second target analyte disposed within or over the second feature 32. The first target analyte may be different from the second target analyte. The first target analyte and second target analyte may include nucleic acids having different sequences.

Figure 5B:
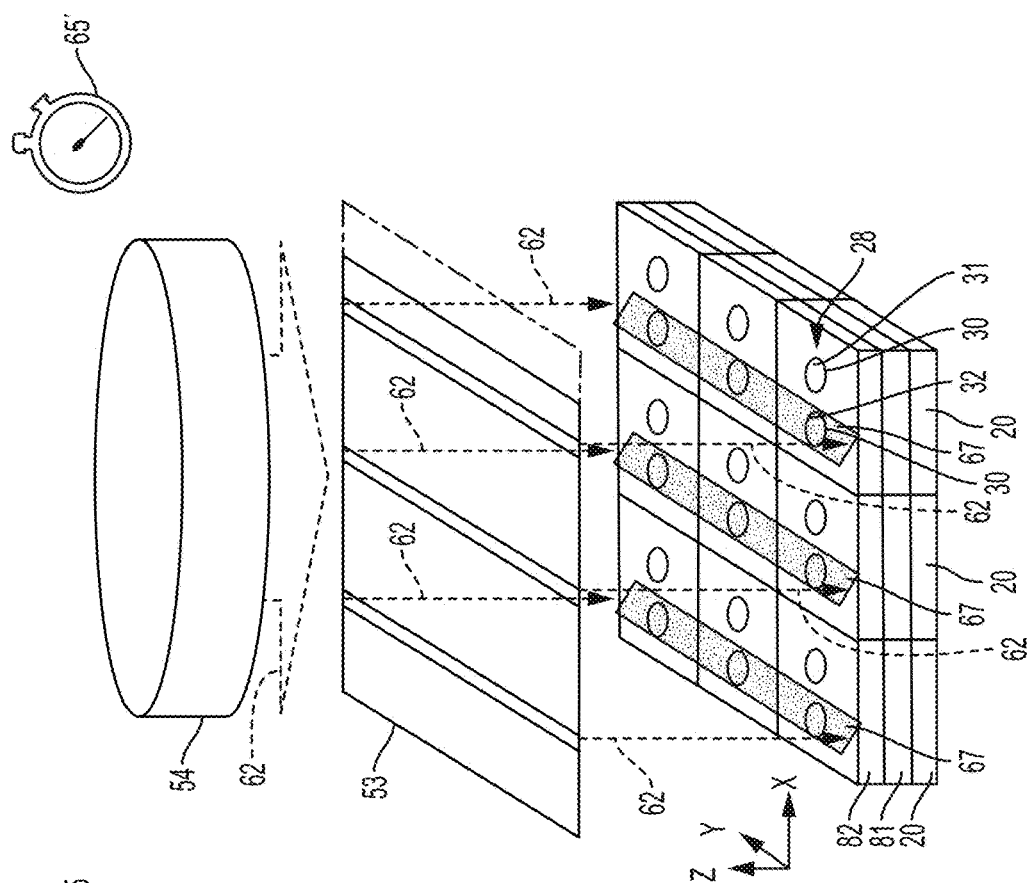
FIG. 5B is schematic perspective view of the example of the portion of the device shown in FIG. 5A at a second time according to the present disclosure.
Figure 5A:
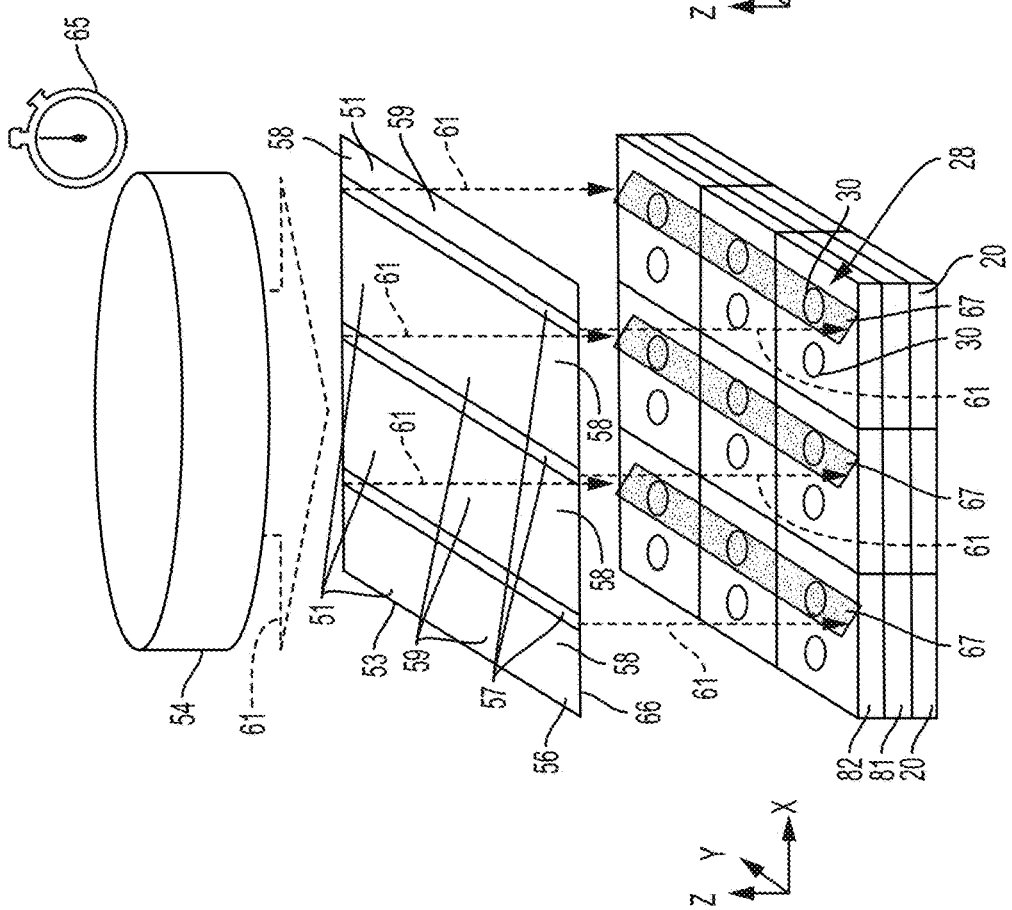
FIG. 5A is schematic perspective view of an example of a portion of a device shown at a first time according to the present disclosure.

In the example depicted in FIG. 5A and FIG. 5B, the mask layer 53 includes a grate 56 of alternating, periodically-spaced, light-transmitting regions 57 and opaque regions 58. The light-transmitting regions 57 are defined by parallel strips 51 of a mask absorber 59 disposed on a mask substrate 66. The portion of the first photons 61 and the portion of the second photons 62 are transmitted through the light-transmitting regions 57 to illuminate parallel illumination stripes 67 on the formation 28 of features 30.

In examples of the present disclosure, the mask absorber 59 may be a thin metallic coating disposed on the mask substrate 66. By way of example, and without limitation, the mask absorber 59 may be chromium, aluminum, iron oxide, titanium, or a silver halide emulsion. It is to be understood that in the mask layer 53 of the present disclosure, the light transmitting regions 57, and the opaque regions are fixed with respect to the mask layer 53. The mask layer 53 is moved using the mask layer actuator 55. Moving the mask layer 53, rather than individually opening and closing pixels, may be advantageous.

Figure 6B:
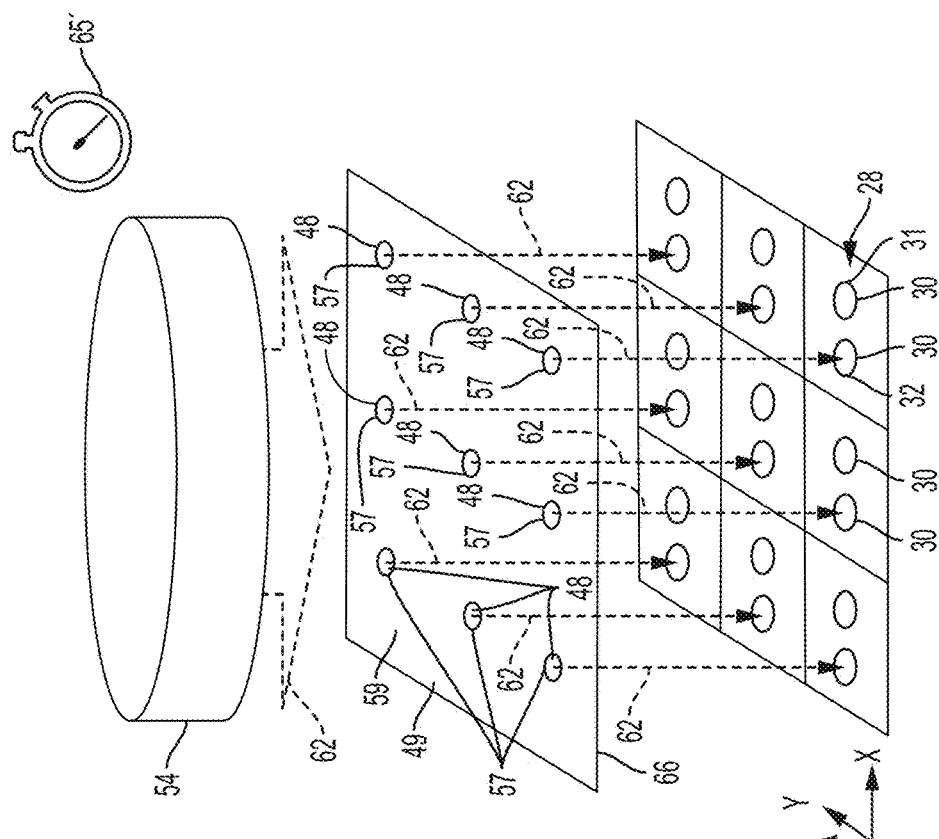
FIG. 6B is schematic perspective view of the further example of the portion of the device shown in FIG. 6A at a second time according to the present disclosure.
Figure 6A:
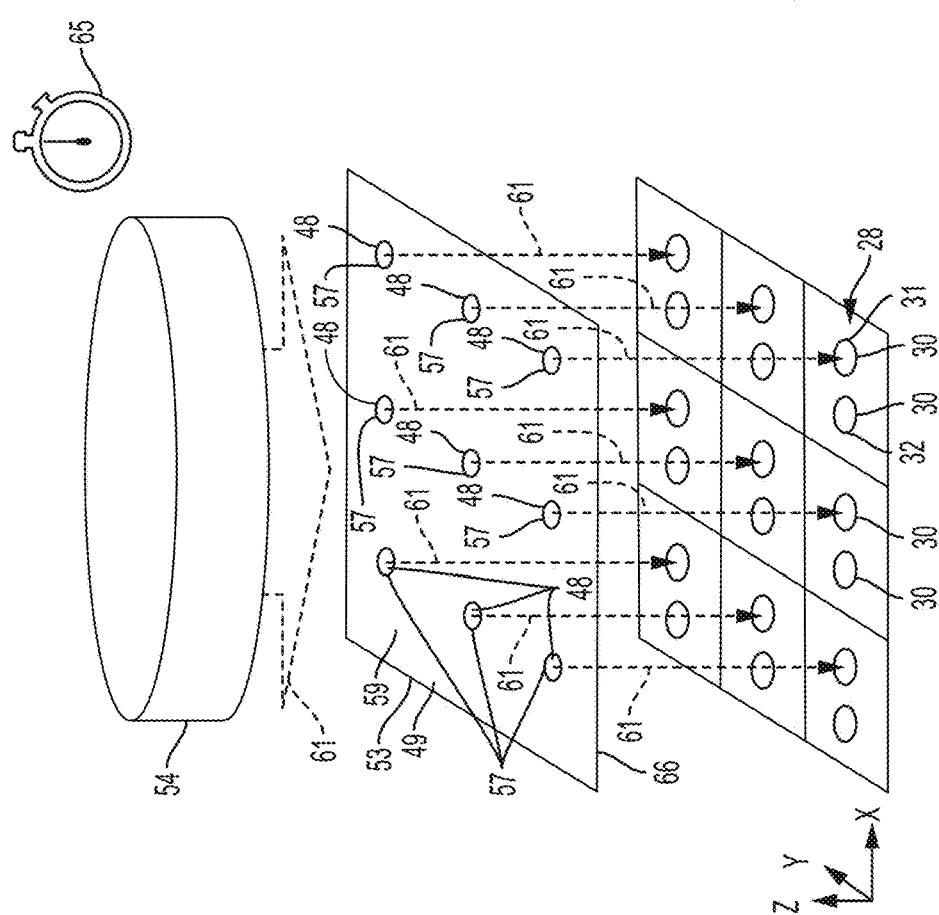
FIG. 6A is schematic perspective view of a further example of a portion of a device shown at a first time according to the present disclosure.

In the example depicted in FIG. 6A and FIG. 6B, the mask layer 53 includes a two-dimensional arrangement of periodically-spaced, light-transmitting regions 57 defined on an opaque field region 49. The opaque field region 49 is defined by a mask absorber 59 disposed on a mask substrate 66. The light-transmitting regions 57 are zones 48 of the mask substrate 66 defined in the opaque field region 49. The zones 48 have the mask absorber 59 excluded from being disposed thereon. It is to be understood that, alternatively, the mask absorber 59 may be removed from the zones 48 after the mask absorber 59 has been deposited on the zones 48. The first photons 61 (FIG. 6A) and the second photons 62 (FIG. 6B) are transmitted through the light-transmitting regions 57 to illuminate corresponding features on the formation 28 of features 30.

For example, the device can include a first luminophore disposed within or over the first feature and a second luminophore disposed within or over the second feature. Illustratively, the device can include a first target analyte disposed within or over the first feature and a second target analyte disposed within or over the second feature, wherein the first target analyte is different from the second target analyte. Optionally, the first target analyte and second target analyte can include nucleic acids having different sequences.

In some embodiments, the first pixel 21 can selectively receive luminescence emitted by the first luminophore 41 responsive to the first photons 61 at the first time, and can selectively receive luminescence emitted by the second luminophore 42 responsive to the second photons 62 at the second time. For example, the structured illumination source 50 may selectively excite the first luminophore relative to the second luminophore. In FIG. 5A and FIG. 5B, the parallel illumination stripes 67 are depicted as transparent bars to schematically illustrate illuminated regions. The illumination stripes 67 may have a uniform intensity distribution, or a gradient intensity distribution of transverse locations in the illumination stripes 67. For example, the illumination stripes 67 may have less intensity at the edges of the illustrated illumination stripes 67 compared to a more intense portion of the illumination stripes 67 along the axial centerline of the illumination stripes 67. It can be seen that the first photons 61 generate a spatial pattern of field strengths (intensity) that is significantly more intense at the first feature 31 than at the second feature 32, and thus can selectively excite the first luminophore 41 relative to the second luminophore 42 at the first time (FIG. 5A). As such, the imaging pixel 20 can generate an electrical signal at the first time that substantially corresponds to selective excitation of the first luminophore 41 disposed within or over the first feature 31. It can also be seen that the second photons 62 generate a spatial pattern of field strengths that is significantly more intense at the second feature 32 than at the first feature 31, and thus can selectively excite the second luminophore 42 relative to the first luminophore 41 at the second time (FIG. 5B). As such, the imaging pixel 20 can generate an electrical signal at the second time that substantially corresponds to selective excitation of the second luminophore 42 disposed within or over the second feature 32. Accordingly, two or more luminophores 40 that are within the detection zone of a particular imaging pixel 20 can be distinguished from each other using spatial patterns of excitation light applied to the luminophores 40 at different times. This combination of spatial and temporal separation of excitation events can allow the imaging pixel 20 to distinguish the two or more luminophores 40 within the detection zone of the imaging pixel 20.

It also should be appreciated that any suitable number of sites can be provided per imaging pixel 20. A device 10 having four sites per imaging pixel is illustrated in FIG. 1C and FIGS. 7A-7D. In some examples, a third feature 33 of the formation 28 of features 30 may be disposed over the first pixel 21 and spatially displaced from each of the first features 31 and the and second features 32. A third luminophore may be disposed within or over the third feature 33. The third luminophore is not particularly shown in the Figs., however, it is to be understood that the third luminophore would be illustrated similarly to the first luminophore 41 and the second luminophore 42, except being disposed within or over the third feature 33. The structured illumination source 50 may be to direct at least a portion of third photons 63 to the third feature 33 at a third time, the third time being different from the first time and second time. The third time is indicated by watch face 65" in FIG. 7C. The first pixel 21 is to selectively receive luminescence emitted by the third luminophore responsive to the portion of the third photons 63 at the third time.

Similarly, a fourth feature 34 of the formation 28 of features 30 may be disposed over the first pixel 21 and spatially displaced from each of the first feature 31, the second feature 32, and the third feature 33. A fourth luminophore may be disposed within or over the fourth feature 34. The fourth luminophore is not particularly shown in the Figs., however, it is to be understood that the fourth luminophore would be illustrated similarly to the first luminophore 41 and the second luminophore 42, except being disposed within or over the fourth feature 34. The structured illumination source 50 may be to direct at least a portion of fourth photons 64 to the fourth feature 34 at a fourth time, the fourth time being different from the first time, second time, and third time. The fourth time is indicated by watch face 65''' in FIG. 7D. The first pixel 21 is to selectively receive luminescence emitted by the fourth luminophore responsive to the portion of the fourth photons 64 at the fourth time.

Figure 7A:
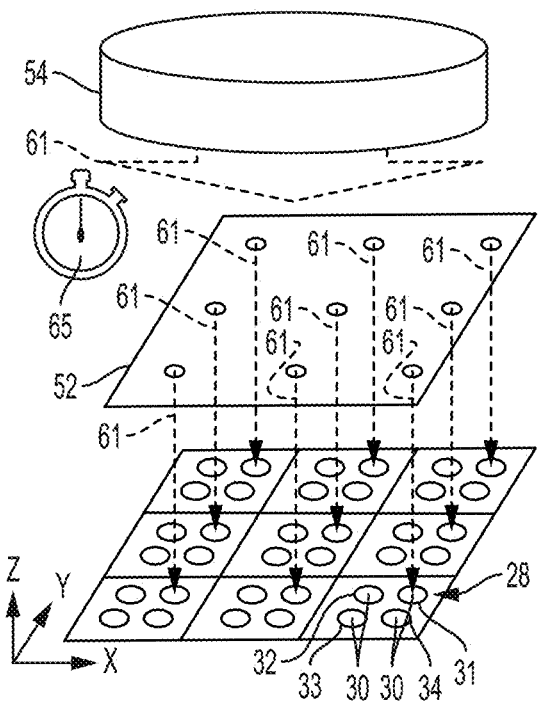
FIG. 7A is schematic perspective view of yet another example of a portion of a device shown at a first time according to the present disclosure.
Figure 7B:
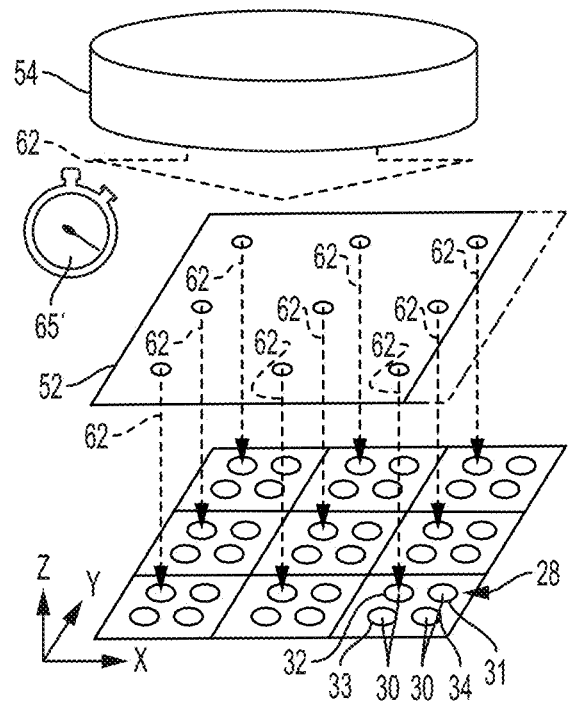
FIG. 7B is schematic perspective view of the example of the portion of the device shown in FIG. 7A at a second time according to the present disclosure.
Figure 7C:
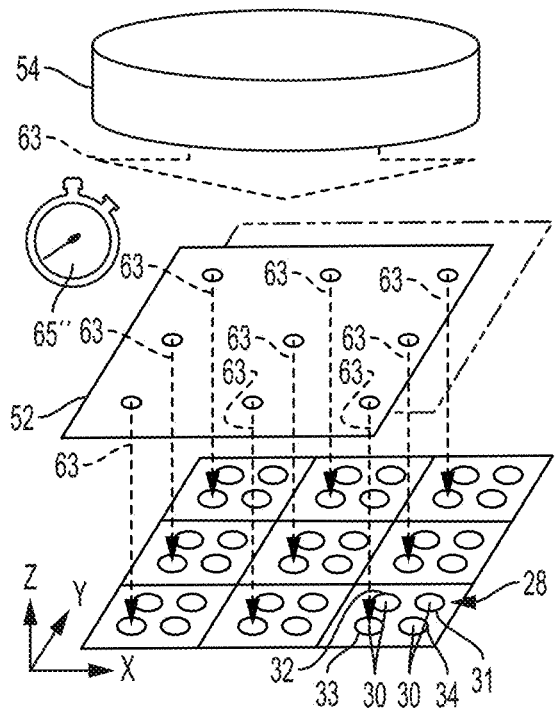
FIG. 7C is schematic perspective view of the example of the portion of the device shown in FIG. 7A at a third time according to the present disclosure.
Figure 7D:
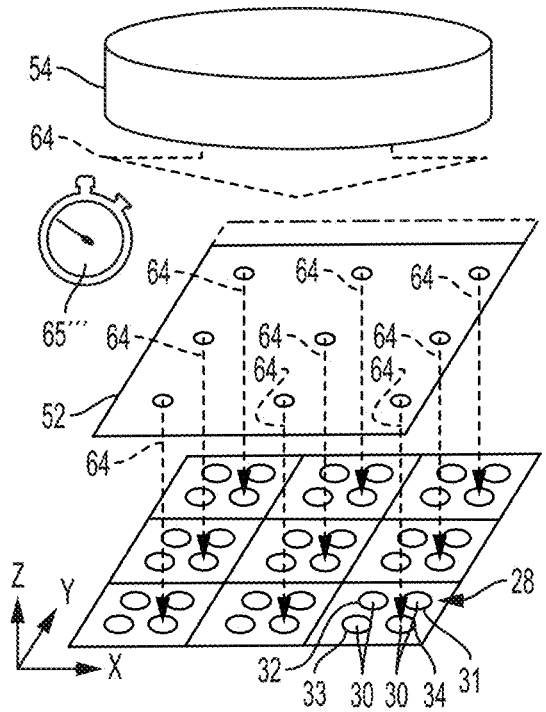
FIG. 7D is schematic perspective view of the example of the portion of the device shown in FIG. 7A at a fourth time according to the present disclosure.

FIGS. 7A-7D respectively schematically illustrate perspective views of examples of selective excitation of first, second, third, and fourth sites within a formation 28 of features 30 such as provided herein and illustrated in FIGS. 7A-7D using a structured illumination source 50 generating photons at selected features at different times. For example, in a manner such as illustrated in FIG. 7A, at a first time, the illumination pattern generator 52 can be irradiated with first photons 61 so as to selectively excite a first site disposed over each imaging pixel 20. Subsequently, in a manner such as illustrated in FIG. 7B, at a second time, illumination pattern generator 52 can be irradiated with second photons 62 so as selectively to excite a second site disposed over each imaging pixel 20. Subsequently, in a manner such as illustrated in FIG. 7C, at a third time, illumination pattern generator 52 can be irradiated with third photons 63 so as to selectively excite a third site disposed over each imaging pixel 20. Subsequently, in a manner such as illustrated in FIG. 7D at a fourth time, illumination pattern generator 52 can be irradiated with fourth photons 64 so as to selectively excite a fourth site disposed over each imaging pixel 20. The imaging pixels 20 respectively can generate electrical signals at the first, second, third, and fourth times, based upon which the first, second, third, and fourth sites disposed over such imaging pixels 20 can be distinguished from one another.

Figure 8A:
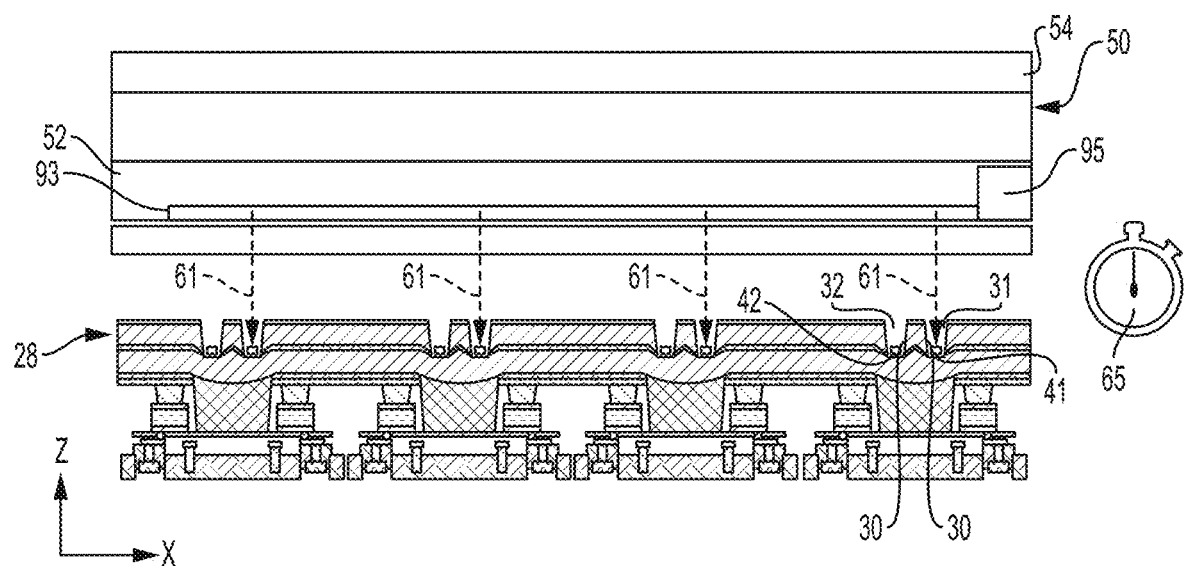
FIG. 8A is a schematic cross-sectional side view of another example of a device shown at a first time according to the present disclosure.
Figure 8B:
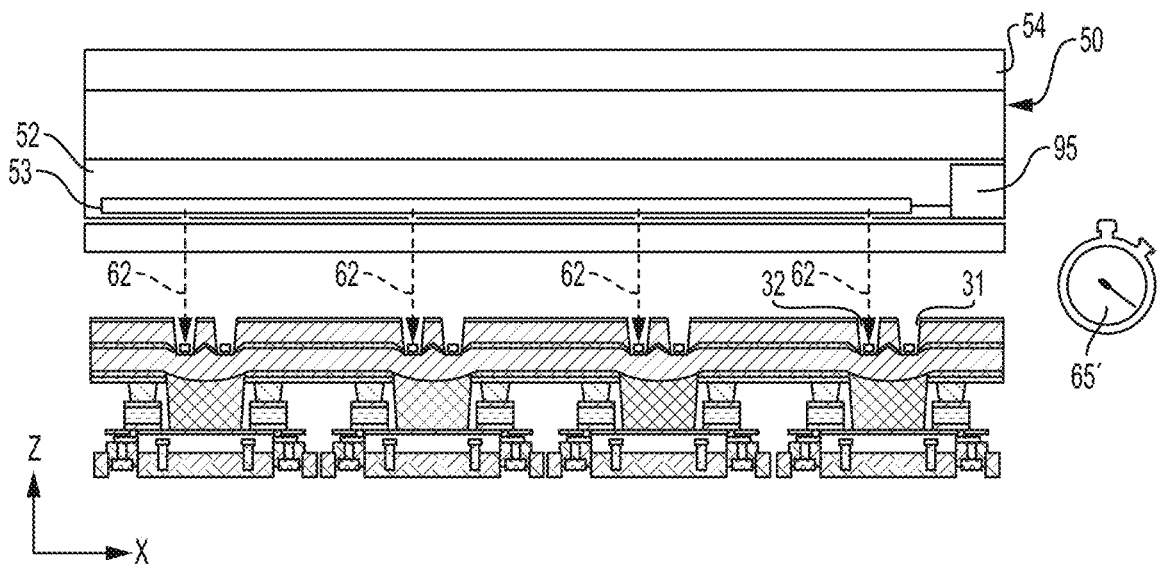
FIG. 8B is a schematic cross-sectional side view of the example of the device shown in FIG. 8A at a second time according to the present disclosure.

FIG. 8A is a schematic cross-sectional side view of an example of a device 10 of the present disclosure. FIG. 8A is similar to FIG. 2A except FIG. 8A depicts schematic details of an example of a structured illumination source 50. As depicted in FIG. 8A, in examples of the device 10, the illumination pattern generator 52 may include an interference pattern generator 93 to propagate light defining a multi-beam interference pattern on the formation 28 of features 30. The illumination pattern generator actuator may include an interference pattern generator actuator 95 connected to the interference pattern generator 93 to change a positional state or rotational state of the interference pattern generator 93 to cause the interference pattern to translate or rotate relative to the formation 28 of features 30. In examples, the positional state of the interference pattern generator 93 may be a position of the interference pattern generator 93 relative to the formation 28 of features 30 as depicted in FIG. 8A and FIG. 8B. As depicted in FIG. 8A, a first position of the interference pattern generator 93 causes the first photons 61 to selectively illuminate the first feature 31. As depicted in FIG. 8B, a second position of the interference pattern generator 93 causes the second photons 62 to selectively illuminate the second feature 32. In other examples, the positional state of the interference pattern generator 93 may be any position of a component of the interference pattern generator 93, actuatable by the interference pattern generator actuator 95, that causes the interference pattern to translate or rotate relative to the formation 28 of features 30. For example, rotation, bending, stretching or compression of a component of the interference pattern generator 93 caused by the interference pattern generator actuator 95 may cause a change in the interference pattern to translate or rotate relative to the formation 28 of features 30.

In the example depicted in FIG. 8A, a first positional state or rotational state of the interference pattern generator 93 causes the portion of the first photons 61 to selectively illuminate the first feature 31. In the example depicted in FIG. 8B, a second positional state or rotational state of the interference pattern generator 93 causes the portion of the second photons to selectively illuminate the second feature 32. It is to be understood that, in FIG. 8A and FIG. 8B, the arrowheads of the dashed arrows with reference numerals 61 and 62 indicate locations of maximum intensity of the interference pattern. The interference pattern may have other maxima and minima along the arrows. Interference patterns and their generation are discussed further herein.

FIG. 9A and FIG. 9B are schematic diagrams depicting the selectivity of multi-beam interference patterns. In the example depicted in FIG. 9A, the multi-beam interference pattern is a two-beam interference pattern. The interference pattern generator is to project parallel linear interference fringes 91, 91' on the formation 28 of features 30. The parallel linear interference fringes 91, 91' have a predetermined periodicity 92 equal to a pixel spacing 94. It is to be understood that FIG. 9A depicts the interference fringes 91 from the first time (indicated by the watch face 65), and the interference fringes 91' from the second time (indicated by the watch face 65'). As such, it is to be understood that the interference fringes 91 and 91' are not projected simultaneously in examples of the present disclosure.

In the example depicted in FIG. 9B, the multi-beam interference pattern is an interference pattern from at least four interfering beams. The interference pattern is a two-dimensional interference pattern having interference maxima 73, 73', 73'', 73''' with a predetermined periodicity 92' equal to a pixel spacing 94. It is to be understood that FIG. 9B depicts the interference maxima 73 from the first time (indicated by the watch face 65); the interference maxima 73' from the second time (indicated by the watch face 65'); the interference maxima 73'' from the first time (indicated by the watch face 65''); and the interference maxima 73''' from the second time (indicated by the watch face 65'''). As such, it is to be understood that the interference maxima 73, 73', 73'' and 73''' are not projected simultaneously in examples of the present disclosure. As demonstrated in the example depicted in FIG. 9B, "periodicity" means the center-to-center spacing of the interference maxima 73, 73', 73'', 73'''.

FIG. 10A is a schematic diagram that illustrates certain geometry and terminology relating to interference. FIG. 10B is a simplified version of FIG. 10A that also includes a depiction of the interference fringes 91''. FIG. 10A illustrates the geometry of a "double-slit" demonstration of interference, similar to Young's double-slit experiment. $r_1$ is a distance from $s_1$ to point P (path length). $r_2$ is a distance from $s_2$ to point P (path length). d is the distance between the centers of the slits. L is the distance between the barrier and the screen. Y is the height above the centerline QO. $\Theta$ is the angle between QO and QP. $\delta$ is the path difference. Reference numeral 76 indicates a coherent beam of light having wavelength $\lambda$. The coherent beam of light 76 is split into two coherent beams (both having wavelength $\lambda$) by the slits $s_1$ and $s_2$ in the barrier. The difference between $r_1$ and $r_2$ causes the light waves to reach the point P at different phases at a particular time. Assuming $r_1$ and $r_2$ are nearly parallel, $\delta = r_2 - r_1 = d \sin \Theta$. Bright fringes are located by the following equation: $\delta = d \sin \Theta_{bright} = m \lambda$; and dark fringes are located by the following equation: $\delta = d \sin \Theta_{dark} = (m+\frac{1}{2})\lambda$. Rearranging, $\sin \Theta_{bright} = m \lambda/d$; and $\sin \Theta_{dark} = (m+\frac{1}{2})\lambda/d$. The order number m=(0, +/−1, +/−2, +/−3, . . . ). Thus, the distance between the fringes is proportional to the ratio ($\lambda/d$) of the wavelength $\lambda$ to the distance between the centers of the slits d.

FIG. 11 is a schematic diagram that applies the interference relationships of the "double-slit" demonstration of FIG. 10A to a diffraction grating having a many slits. FIG. 12 is a schematic diagram that depicts the relative intensity of orders m produced by a coherent beam of light 76 diffracted by a diffraction grating.

Figure 13A:
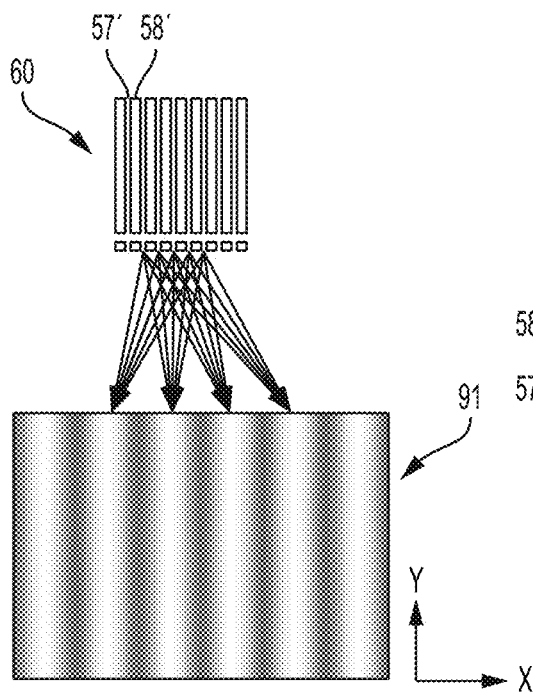
FIG. 13A and FIG. 13B are schematic diagrams depicting interference fringes that are produced by a diffraction grating.
Figure 13B:
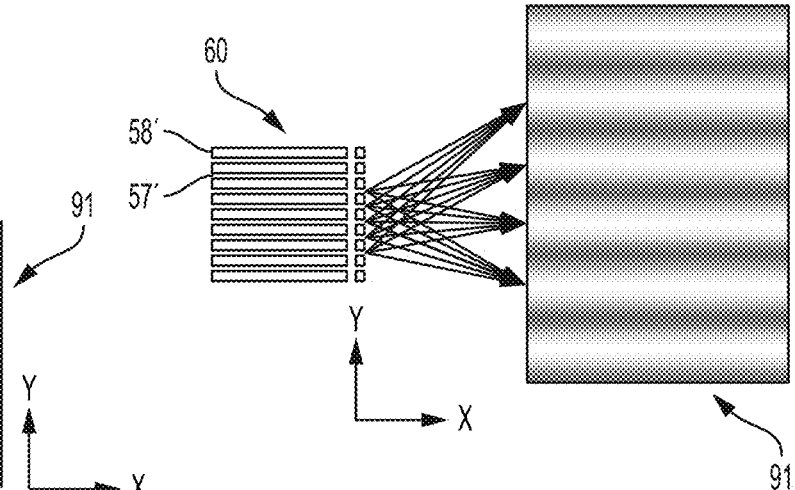
Figure 13C:
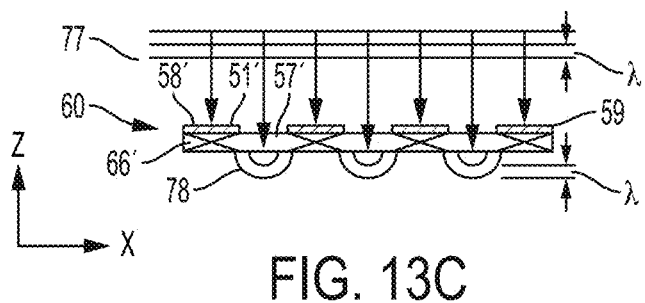
FIG. 13C is a schematic, cross-sectional view of an example of the diffraction grating 60 shown in FIG. 13A.
Figure 13D:
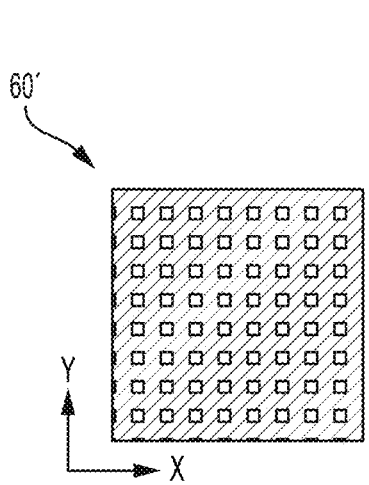
FIG. 13D is a schematic view of a two-dimensional diffraction grating formed from the orthogonal diffraction gratings depicted in FIG. 13A and FIG. 13B superimposed upon one another.
Figure 13E:
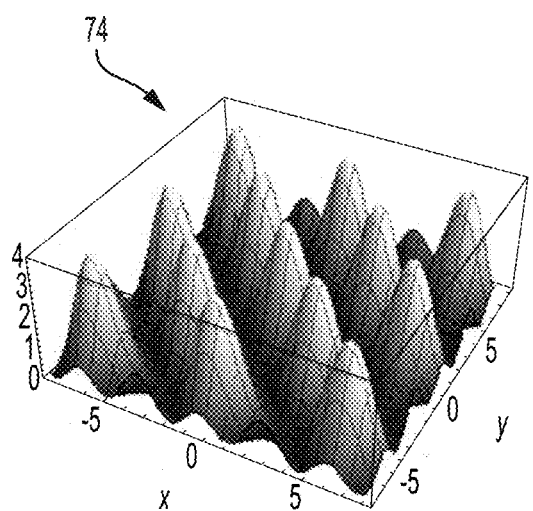
FIG. 13E is a schematic diagram depicting an interference intensity distribution produced by a two-dimensional diffraction grating as shown in FIG. 13D.

FIG. 13A and FIG. 13B are schematic diagrams depicting interference fringes 91 that are produced by a diffraction grating 60. The diffraction grating 60 has alternating, periodically-spaced, light-transmitting regions 57' and opaque regions 58'. FIG. 13C is a schematic, cross-sectional view of an example of the diffraction grating 60 shown in FIG. 13A. The light-transmitting regions 57' are defined by parallel strips 51' of a mask absorber 59 disposed on a transparent substrate 66'. The diffraction grating 60 depicted in FIG. 13C is a binary diffraction grating because light is either transmitted through the light-transmitting regions 57' or light is blocked from entering the opaque regions 58'. A coherent wavefront 77 produces coherent wavelets 78 exiting each light-transmitting region 57'. The interference fringes 91 depicted in FIG. 13A and FIG. 13B are parallel to the light-transmitting regions 57'. FIG. 13D is a schematic view of a two-dimensional diffraction grating 60' formed from the orthogonal diffraction gratings 60 depicted in FIG. 13A and FIG. 13B superimposed upon one another. FIG. 13E is a schematic diagram depicting an interference intensity distribution 74 produced by a two-dimensional diffraction grating 60' as shown in FIG. 13D.

Figure 14:
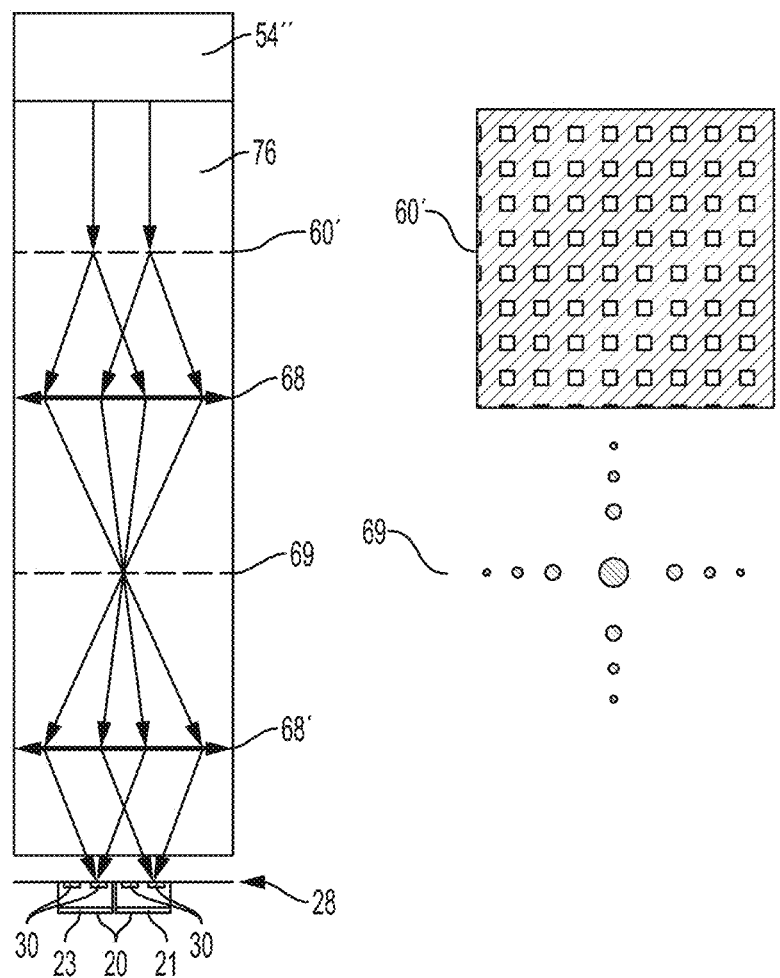
FIG. 14 is a schematic diagram of an example of a device according to the present disclosure.

FIG. 14 is a schematic diagram of an example of a device 10 according to the present disclosure. A laser 54" produces a coherent beam of light 76. A two-dimensional diffraction grating 60' splits the coherent beam of light 76 into a set of interfering beams. A lens 68 directs the set of interfering beams to a beam blocker 69 which blocks zero order, second and higher order beams, and passes first order beams in the x/y axis. A second lens 68' directs the first order beams to the formation 28 of features 30. The coherent beam of light 76 may be shifted, or the two-dimensional diffraction grating 60' may be shifted to illuminate each of the features 30 (one feature 30 per imaging pixel 20 at any particular time) disposed over the imaging pixels 20. The coherent light beam 76 or the two-dimensional diffraction grating 60' may be shifted by a piezoelectric actuator. A plurality of features 30 corresponds to each imaging pixel 20. In FIG. 14, two features 30 are shown corresponding to the first pixel 21 and two features 30 are shown corresponding to the second pixel 23. However, as stated herein, examples of the present disclosure may include any number of features 30 greater than one disposed over each imaging pixel 20, e.g., 2, 3, 4, 5, 6, 7, 8 or more features may be disposed over each imaging pixel 20.

Figure 15A:
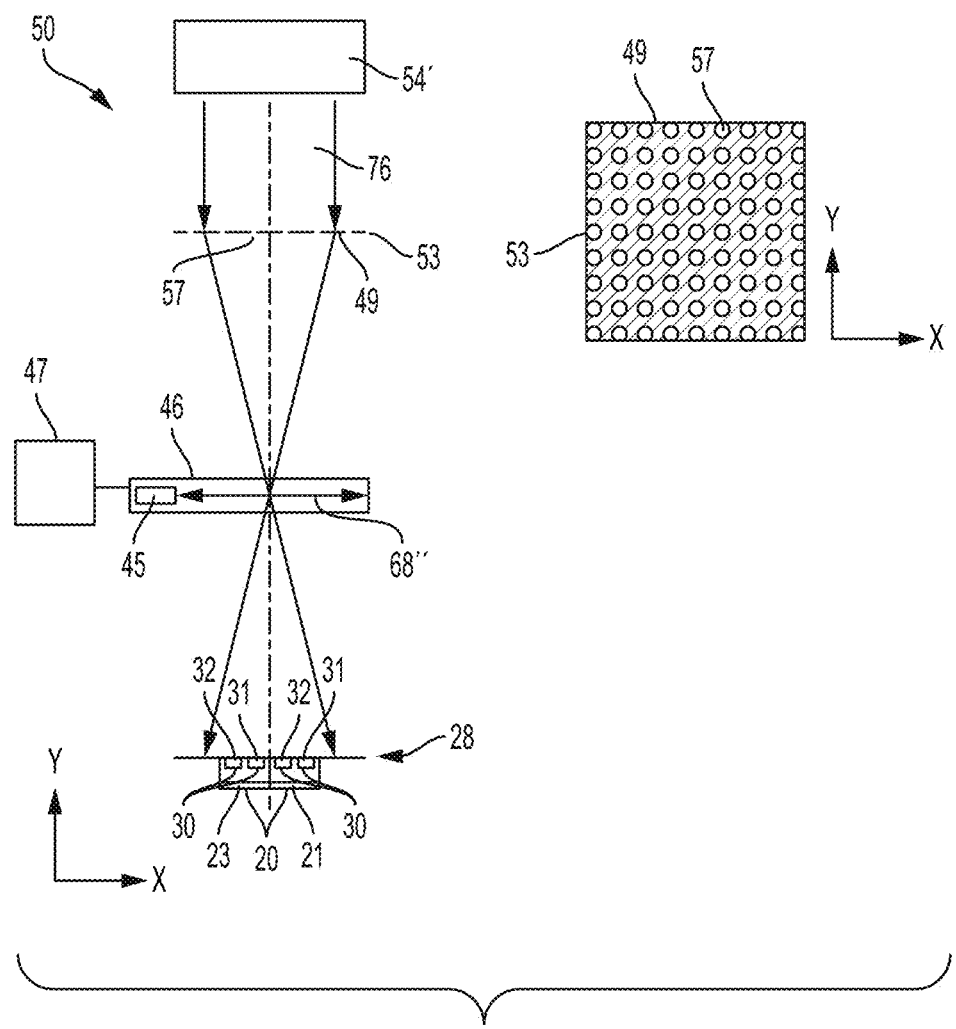
FIG. 15A is a schematic diagram of another example of a device according to the present disclosure.
Figure 15B:
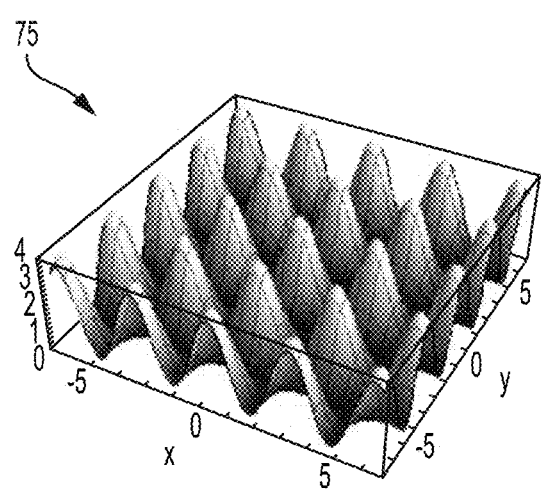
FIG. 15B is an intensity distribution of a representative dotted pattern of light on the formation of features of the example of the device depicted in FIG. 15A according to the present disclosure.

FIG. 15A is a schematic diagram of a device 10 according to the present disclosure. An LED 54' (or white light with a band pass filter) produces a beam of light. A mask layer 53 includes a two-dimensional arrangement of periodically-spaced, light-transmitting regions 57 defined on an opaque field region 49. The portion of the first photons 61 (FIG. 6A) and the portion of the second photons 62 (FIG. 6B) are transmitted through the light-transmitting regions 57 to illuminate corresponding features on the formation 28 of features 30. In examples of the present disclosure, the structured illumination source 50 may include an optical component 46. The device 10 may further include a controller 47 coupled to the optical component 46 to control the optical component 46 so as to direct the portion of the first photons in the illumination pattern to the first feature 31 at the first time and to direct the portion of the second photons in the illumination pattern to the second feature 32 at the second time. In an example, the optical component 46 may include a beam steering component 45. The mask layer 53 passes a dotted pattern of light to a projection lens set 68". The projection lens set 68" is a portion of the optical component 46. The projection lens set 68" projects the dotted pattern of light onto the formation 28 of features 30. The mask layer 53 may be shifted to illuminate each of the features 30 (one feature 30 per imaging pixel 20 at any particular time) disposed over the imaging pixels 20. The mask layer 53 may be shifted by e.g., a piezoelectric actuator. A plurality of features 30 corresponds to each imaging pixel 20. In FIG. 15A, two features 30 are shown corresponding to the first pixel 21 and two features 30 are shown corresponding to the second pixel 23. However, as stated herein, examples of the present disclosure may include any number of features 30 greater than one disposed over each imaging pixel 20, e.g., 2, 3, 4, 5, 6, 7, 8 or more features may be disposed over each imaging pixel 20. The features 30 may be arranged in any suitable formation 28. For example the formation 28 of features 30 may be in rows and columns, a row, a column, triangular clusters, hexagonal clusters, etc. As such, the piezoelectric actuator may be capable of actuating the mask layer 53 in X and Y directions. FIG. 15B is an intensity distribution 75 of a representative dotted pattern of light on the formation 28 of features 30 of the example of the device 10 depicted in FIG. 15A according to the present disclosure.

Figure 16:
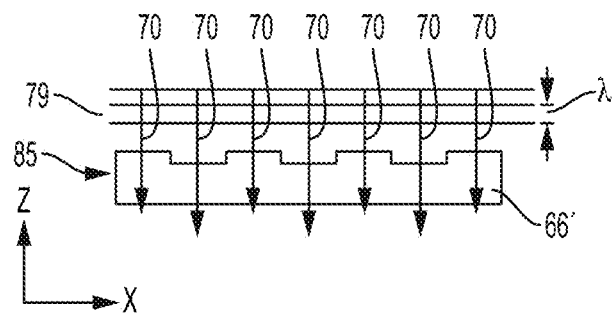
FIG. 16 is a schematic cross-sectional view of an example of a two-dimensional transmission phase mask.

In examples of the present disclosure, the interference pattern generator 93 may include a two-dimensional transmission phase mask 85 to split a laser beam into a set of interfering beams. FIG. 16 is a schematic cross-sectional view of an example of a two-dimensional transmission phase mask 85. Unlike the binary diffraction grating 60 shown in FIG. 13C, the two-dimensional transmission phase mask 85 does not have opaque regions. The two-dimensional transmission phase mask 85 splits the coherent laser beam into interfering beams by having an undulating profile and thickness defined on a transparent substrate 66'. As depicted in FIG. 16, a coherent incident beam 79 is split into child beams 70 as the light traveling through the transmitting regions has phase variation induced into the child beams 70 by the undulation of the surface and thickness of the two-dimensional transmission phase mask 85.

Figure 17A:
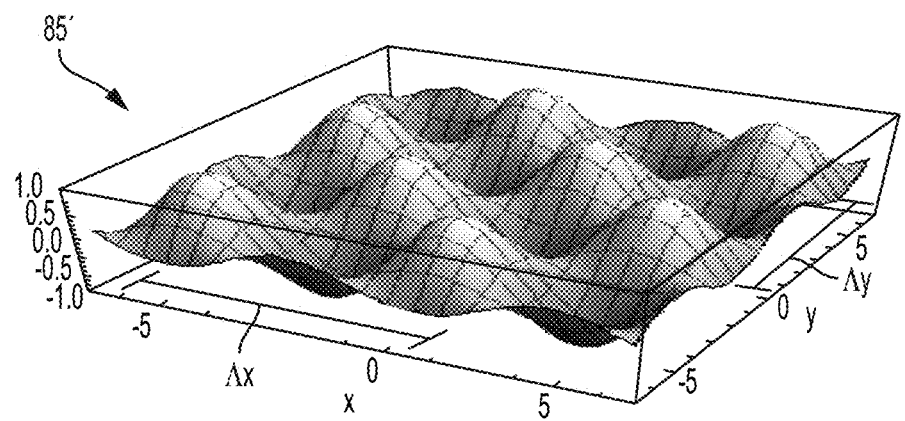
FIG. 17A is a perspective view of another example of a two-dimensional transmission phase mask.
Figure 17B:
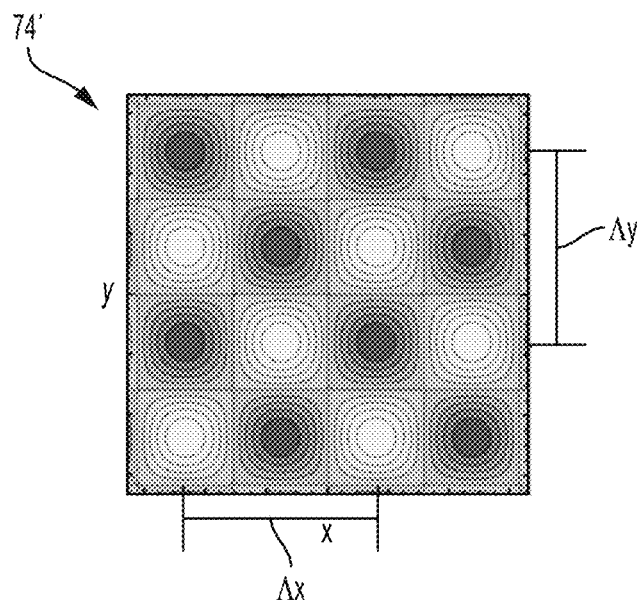
FIG. 17B is an example of an intensity contour plot depicting an interference intensity distribution produced using the two-dimensional transmission phase mask depicted in FIG. 17A.

FIG. 17A is a perspective view of another example of a two-dimensional transmission phase mask 85'. The surface of the two-dimensional transmission phase mask 85' depicted in FIG. 17A is defined by a two-dimensional sinusoidal pattern with a wavelength $\Lambda x$ parallel to the x-axis and a wavelength $\Lambda y$ parallel to the y-axis. FIG. 17B is an example of an intensity contour plot depicting an interference intensity distribution 74' produced using the two-dimensional transmission phase mask 85' depicted in FIG. 17A. In the example of the intensity contour plot depicted in FIG. 17B, the two-dimensional interference pattern has intensity wavelengths equal to the wavelengths $\Lambda x$ and $\Lambda y$.

The present compositions, devices, and methods suitably can be used so as to generate luminescent images in SBS sequencing. For example, the device further can include at least one microfluidic feature in contact with the formation 28 of features 30 and to provide a flow of one or more analytes to the formation 28 of features 30. As still another example, referring again to the illustrative examples described with reference to FIGS. 7A-7D, the first luminophore 41 can be coupled to a first nucleic acid, the second luminophore 42 can be coupled to a second nucleic acid, the third luminophore can be coupled to a third nucleic acid, and the fourth luminophore can be coupled to a fourth nucleic acid. For example, in compositions for use in sequencing DNA using luminescent imaging, the first luminophore 41 can be coupled to A, the second luminophore 42 can be coupled to G, the third luminophore can be coupled to C, and the fourth luminophore can be coupled to T. As another example, in compositions for use in sequencing RNA using luminescent imaging, the first luminophore 41 can be coupled to A, the second luminophore 42 can be coupled to G, the third luminophore can be coupled to C, and the fourth luminophore can be coupled to U.

In examples of the device 10 disclosed herein, the first luminophore 41 can be coupled to a first polynucleotide to be sequenced, and the second luminophore 42 can be coupled to a second polynucleotide to be sequenced. For example, the first polynucleotide can be coupled to the first feature 31, and the second polynucleotide can be coupled to the second feature 32. The device can further include a first polymerase adding a first nucleic acid to a third polynucleotide that is complementary to and coupled to the first polynucleotide, the first nucleic acid being coupled to the first luminophore. The device further can include a second polymerase adding a second nucleic acid to a fourth polynucleotide that is complementary to and coupled to the second polynucleotide, the second nucleic acid being coupled to the second luminophore 42. The device further can include a channel flowing a first liquid including the first and second nucleic acids and the first and second polymerases into or over the first and second features. For example, the first and second polynucleotides can be coupled to the first feature 31 and the second feature 32 that are disposed over a first pixel 21, and that are to be sequenced using a suitable SBS scheme. The first luminophore 41 and the second luminophore 42 respectively can be coupled to first and second nucleic acids that respectively are being incorporated into the first and second polynucleotides, e.g., using the first and second polymerases. Following an SBS step of incorporating the first and second nucleic acids into the first and second polynucleotides, the first luminophore 41 and the second luminophore 42 can be selectively luminescently imaged at different times than one another in a manner such as provided herein, so as to obtain respective electrical signals responsive to presence of the first luminophore 41 at the first polynucleotide (that is, incorporation of the first nucleic acid into the first polynucleotide) and responsive to presence of the second luminophore 42 at the second polynucleotide (that is, incorporation of the second nucleic acid into the second polynucleotide).

Figure 18A:
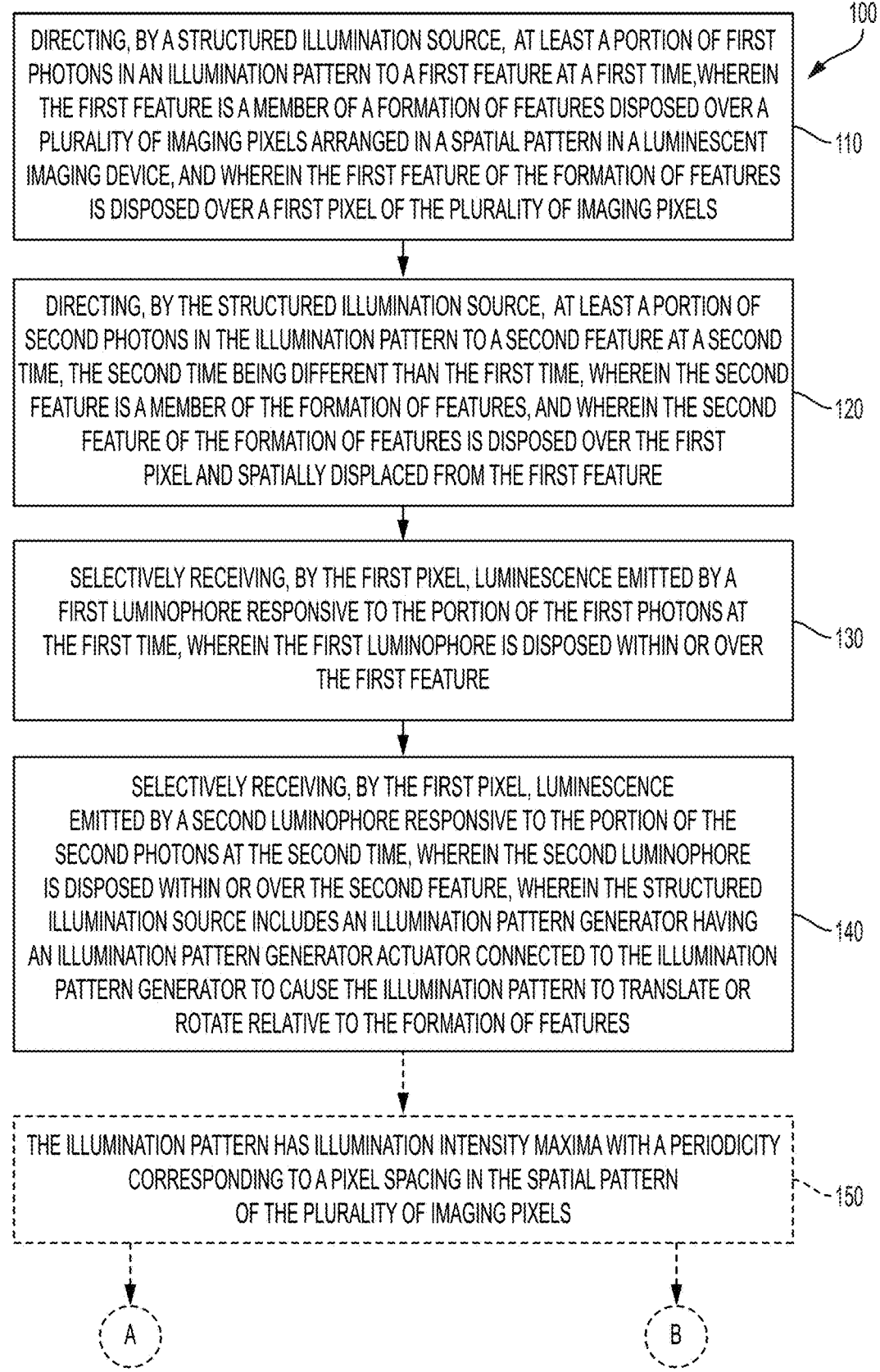

FIGS. 18A-18C together are a flow diagram depicting an example of a method 100 according to the present disclosure. As depicted at block 110, the method 100 includes "directing, by a structured illumination source, at least a portion of first photons in an illumination pattern to a first feature at a first time, wherein the first feature is a member of a formation of features disposed over a plurality of imaging pixels arranged in a spatial pattern in a luminescent imaging device, and wherein the first feature of the formation of features is disposed over a first pixel of the plurality of imaging pixels."

The method 100 further includes "directing, by the structured illumination source, at least a portion of second photons in the illumination pattern to a second feature at a second time, the second time being different from the first time, wherein the second feature is a member of the formation of features, and wherein the second feature of the formation of features is disposed over the first pixel and spatially displaced from the first feature" as shown at block 120.

The method 100 further includes "selectively receiving, by the first pixel, luminescence emitted by a first luminophore responsive to the portion of the first photons at the first time, wherein the first luminophore is disposed within or over the first feature" as shown at block 130.

The method 100 further includes "selectively receiving, by the first pixel, luminescence emitted by a second luminophore responsive to the portion of the second photons at the second time, wherein the second luminophore is disposed within or over the second feature, wherein the structured illumination source includes an illumination pattern generator actuator having an illumination pattern generator actuator connected to the illumination pattern generator to cause the illumination pattern to translate or rotate relative to the formation of features" as shown at block 140.

The dashed lines in FIGS. 18A-18C indicate optional elements of the method 100. For example, "the illumination pattern has illumination intensity maxima with a periodicity corresponding to a pixel spacing in the spatial pattern of the plurality of imaging pixels" shown at block 150, is an optional element connected to block 140. In FIG. 18B, continuation circle "A" connects optional element 160 to block 150 of FIG. 18A. At block 160, the method 100 optionally includes "the illumination pattern generator includes a mask layer and the illumination pattern generator actuator comprises a mask layer actuator connected to the mask layer to translate or rotate the mask layer relative to the formation of features; a first position of the mask layer causes the portion of the first photons to selectively illuminate the first feature; a second position of the mask layer causes the portion of the second photons to selectively illuminate the second feature; the mask layer includes a grate of alternating, periodically-spaced, light-transmitting regions and opaque regions; the light-transmitting regions are defined by parallel stripes of a mask absorber disposed on a mask substrate; and the portion of the first photons and the portion of the second photons are transmitted through the light-transmitting regions to illuminate parallel illumination stripes on the formation of features."

In FIG. 18C, continuation circle "B" connects optional element 170 to block 150 of FIG. 18A. At block 170, the method 100 optionally includes "the illumination pattern generator comprises: an interference pattern generator to propagate light defining a multi-beam interference pattern on the formation of features; wherein the illumination pattern generator actuator comprises an interference pattern generator actuator connected to the interference pattern generator to change a positional state or rotational state of the interference pattern generator to cause the interference pattern to translate or rotate relative to the formation of features."

While various illustrative examples of the present disclosure are explicitly described herein, it will be apparent to one skilled in the art that various changes and modifications may be made therein without departing from the present disclosure. For example, although certain compositions, devices, and methods are discussed herein with reference to luminescent imaging associated with sequencing polynucleotides such as DNA or RNA, it should be understood that the present compositions, devices, and methods suitably can be adapted for use in luminescent imaging associated with any appropriate subject. The appended claims are intended to cover all such changes and modifications that fall within the true spirit and scope of the invention.

Additional Notes

It should be appreciated that all combinations of the foregoing concepts and additional concepts discussed in greater detail herein (provided such concepts are not mutually inconsistent) are contemplated as being part of the subject matter disclosed herein. In particular, all combinations of claimed subject matter appearing at the end of this disclosure are contemplated as being part of the subject matter disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if the value(s) or sub-range(s) within the stated range were explicitly recited. For example, a range from about 300 nm to about 800 nm, should be interpreted to include not only the explicitly recited limits of from about 300 nm to about 800 nm, but also to include individual values, such as about 358 nm, about 425 nm, about 585 nm, about 675.5 nm, etc., and sub-ranges, such as from about 450 nm to about 550 nm, from about 355 nm to about 580 nm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A device, comprising:
 a plurality of imaging pixels arranged in a spatial pattern;
 a formation of features disposed over the plurality of imaging pixels, wherein the features repeat in the spatial pattern in which the plurality of imaging pixels is arranged;
 a first feature of the formation of features, the first feature disposed over a first pixel of the plurality of imaging pixels,
 a second feature of the formation of features, the second feature disposed over the first pixel and spatially displaced from the first feature;
 a first luminophore disposed within or over the first feature;
 a second luminophore disposed within or over the second feature; and
 a structured illumination source to direct at least a portion of first photons in an illumination pattern to the first feature at a first time, and to direct at least a portion of second photons in the illumination pattern to the second feature at a second time, the second time being different from the first time, the first pixel to selectively receive luminescence emitted by the first luminophore responsive to the portion of the first photons at the first time, and to selectively receive luminescence emitted by the second luminophore responsive to the portion of the second photons at the second time, wherein the structured illumination source includes an illumination pattern generator and an illumination pattern generator actuator connected to the illumination pattern generator to cause the illumination pattern to translate or rotate relative to the formation of features, wherein the illumination pattern has illumination intensity maxima with a periodicity corresponding to a pixel spacing in the spatial pattern of the plurality of imaging pixels, wherein the pixel spacing ranges from about 10 nanometers to about 20 micrometers, and wherein the illumination pattern generator includes a mask layer, and wherein the illumination pattern generator actuator comprises a mask layer actuator connected to the mask layer to translate or rotate the mask layer relative to the formation of features.

2. The device of claim 1 wherein the structured illumination source is to flood illuminate the illumination pattern generator with the first photons and the second photons.

3. The device of claim 2 wherein the structured illumination source comprises a laser.

4. The device of claim 1 wherein:
 a first position of the mask layer causes the portion of the first photons to selectively illuminate the first feature; and
 a second position of the mask layer causes the portion of the second photons to selectively illuminate the second feature.

5. The device of claim 1 wherein:
 the mask layer includes a grate of alternating, periodically-spaced, light-transmitting regions and opaque regions;
 the light-transmitting regions are defined by parallel strips of a mask absorber disposed on a mask substrate; and
 the portion of the first photons and the portion of the second photons are transmitted through the light-transmitting regions to illuminate parallel illumination stripes on the formation of features.

6. The device of claim 1 wherein:
 the mask layer includes a two-dimensional arrangement of periodically-spaced, light-transmitting regions defined on an opaque field region;
 the opaque field region is defined by a mask absorber disposed on a mask substrate;
 the light-transmitting regions are zones of the mask substrate defined in the opaque field region, the zones having the mask absorber excluded from being disposed thereon; and
 the portion of the first photons and the portion of the second photons are transmitted through the light-transmitting regions to illuminate corresponding features on the formation of features.

7. The device of claim 1 wherein the illumination pattern generator comprises:
 an interference pattern generator to propagate light defining a multi-beam interference pattern on the formation of features;
 wherein the illumination pattern generator actuator comprises an interference pattern generator actuator connected to the interference pattern generator to change a positional state or rotational state of the interference pattern generator to cause the interference pattern to translate or rotate relative to the formation of features.

8. The device of claim 7 wherein:
a first positional state or rotational state of the interference pattern generator causes the portion of the first photons to selectively illuminate the first feature; and
a second positional state or rotational state of the interference pattern generator causes the portion of the second photons to selectively illuminate the second feature.

9. The device of claim 7 wherein:
the multi-beam interference pattern is a two-beam interference pattern;
the interference pattern generator is to project parallel linear interference fringes on the formation of features; and
the parallel linear interference fringes have a predetermined periodicity equal to a pixel spacing.

10. The device of claim 7 wherein:
the multi-beam interference pattern is an interference pattern from at least four interfering beams; and
the interference pattern is a two-dimensional interference pattern having interference maxima with a predetermined periodicity equal to a pixel spacing.

11. The device of claim 7 wherein the interference pattern generator includes a two-dimensional transmission phase mask to split a laser beam into a set of interfering beams.

12. The device of claim 1 wherein: the structured illumination source comprises an optical component; and the device further comprises a controller coupled to the optical component to control the optical component so as to direct the portion of the first photons in the illumination pattern to the first feature at the first time and to direct the portion of the second photons in the illumination pattern to the second feature at the second time.

13. The device of claim 12 wherein the optical component comprises a beam steering component.

14. The device of claim 1 wherein the second feature is laterally displaced from the first feature.

15. The device of claim 1, further comprising:
a third feature of the formation of features disposed over the first pixel and spatially displaced from each of the first features and second features;
a third luminophore disposed within or over the third feature;
the structured illumination source to direct at least a portion of third photons to the third feature at a third time, the third time being different from the first time and second time; and
the first pixel to selectively receive luminescence emitted by the third luminophore responsive to the portion of the third photons at the third time.

16. The device of claim 15, further comprising:
a fourth feature of the formation of features disposed over the first pixel and spatially displaced from each of the first features, second features, and third features;
a fourth luminophore disposed within or over the fourth feature;
the structured illumination source to direct at least a portion of fourth photons to the fourth feature at a fourth time, the fourth time being different from the first time, second time, and third time; and
the first pixel to selectively receive luminescence emitted by the fourth luminophore responsive to the portion of the fourth photons at the fourth time.

17. The device of claim 1 wherein the first and second photons have wavelengths in a range from about 300 nm to about 800 nm.

18. The device of claim 1 wherein:
the structured illumination source comprises a mirror; and
the device further comprises an actuator coupled to the mirror to rotate the mirror so as to direct the portion of the first photons in the illumination pattern to the first feature at the first time and to direct the portion of the second photons in the illumination pattern to the second feature at the second time.

19. The device of claim 1 wherein:
the structured illumination source comprises a projection lens set; and
the device further comprises an actuator coupled to the projection lens set to rotate the projection lens set so as to direct the portion of the first photons in the illumination pattern to the first feature at the first time and to direct the portion of the second photons in the illumination pattern to the second feature at the second time.

20. A method, comprising:
directing, by a structured illumination source, at least a portion of first photons in an illumination pattern to a first feature at a first time, wherein the first feature is a member of a formation of features disposed over a plurality of imaging pixels arranged in a spatial pattern in a luminescent imaging device, wherein the features repeat in the spatial pattern in which the plurality of imaging pixels is arranged, and wherein the first feature of the formation of features is disposed over a first pixel of the plurality of imaging pixels;
directing, by the structured illumination source, at least a portion of second photons in the illumination pattern to a second feature at a second time, the second time being different from the first time, wherein the second feature is a member of the formation of features, and wherein the second feature of the formation of features is disposed over the first pixel and spatially displaced from the first feature;
selectively receiving, by the first pixel, luminescence emitted by a first luminophore responsive to the portion of the first photons at the first time, wherein the first luminophore is disposed within or over the first feature; and
selectively receiving, by the first pixel, luminescence emitted by a second luminophore responsive to the portion of the second photons at the second time, wherein the second luminophore is disposed within or over the second feature, wherein the structured illumination source includes an illumination pattern generator and an illumination pattern generator actuator connected to the illumination pattern generator to cause the illumination pattern to translate or rotate relative to the formation of features, wherein the illumination pattern has illumination intensity maxima with a periodicity corresponding to a pixel spacing in the spatial pattern of the plurality of imaging pixels, wherein the pixel spacing ranges from about 10 nanometers to about 20 micrometers, wherein the illumination pattern generator includes a mask layer, and wherein the illumination pattern generator actuator comprises a mask layer actuator connected to the mask layer to translate or rotate the mask layer relative to the formation of features.

21. The method of claim 20 wherein:
a first position of the mask layer causes the portion of the first photons to selectively illuminate the first feature;

a second position of the mask layer causes the portion of the second photons to selectively illuminate the second feature;

the mask layer includes a grate of alternating, periodically-spaced, light-transmitting regions and opaque regions;

the light-transmitting regions are defined by parallel strips of a mask absorber disposed on a mask substrate; and the portion of the first photons and the portion of the second photons are transmitted through the light-transmitting regions to illuminate parallel illumination stripes on the formation of features.

22. The method of claim 20 wherein the illumination pattern generator comprises:

an interference pattern generator to propagate light defining a multi-beam interference pattern on the formation of features;

wherein the illumination pattern generator actuator comprises an interference pattern generator actuator connected to the interference pattern generator to change a positional state or rotational state of the interference pattern generator to cause the interference pattern to translate or rotate relative to the formation of features.

23. A device, comprising:

a plurality of imaging pixels arranged in a spatial pattern;

a formation of features disposed over the plurality of imaging pixels, wherein the features repeat in the spatial pattern in which the plurality of imaging pixels is arranged;

an illumination pattern generator including a mask layer;

an illumination pattern generator actuator including a mask layer actuator connected to the mask layer to translate or rotate the mask layer relative to the formation of features;

a first feature of the formation of features, the first feature being disposed over a first pixel of the plurality of imaging pixels; and a second feature of the formation of features, the second feature disposed over the first pixel and spatially displaced from the first feature;

wherein the illumination pattern generator actuator is connected to the illumination pattern generator to cause an illumination pattern having illumination intensity maxima with a periodicity corresponding to a pixel spacing in the spatial pattern of the plurality of imaging pixels to selectively irradiate the first feature with light at a first time;

wherein the illumination pattern generator causes the illumination pattern to selectively irradiate the second feature with light at a second time, the second time being different from the first time;

wherein the illumination pattern has illumination intensity maxima with a periodicity corresponding to a pixel spacing in the spatial pattern of the plurality of imaging pixels;

and wherein the pixel spacing ranges from about 10 nanometers to about 20 micrometers.

24. The device of claim 23, further comprising:

a structured illumination source to generate first photons at the first time, and to generate second photons at the second time;

a first luminophore disposed within or over the first feature and a second luminophore disposed within or over the second feature;

a first target analyte disposed within or over the first feature and a second target analyte disposed within or over the second feature, wherein the first target analyte is different from the second target analyte; and the first target analyte and second target analyte comprise nucleic acids having different sequences.

\* \* \* \* \*